(12) United States Patent
Bhat et al.

(10) Patent No.: US 11,407,993 B2
(45) Date of Patent: Aug. 9, 2022

(54) METHOD FOR THE SYNTHESIS OF DNA CONJUGATES BY MICELLAR CATALYSIS

(71) Applicant: Technische Universität Dortmund, Dortmund (DE)

(72) Inventors: Avinash Shashidhar Bhat, Heidelberg (DE); Mateja Klika Skopic, Dortmund (DE); Andreas Brunschweiger, Dortmund (DE); Ralf Weberskirch, Bochum (DE)

(73) Assignee: Technische Universitaet Dortmund, Dortmund (DE)

( * ) Notice: Subject to any disclaimer, the term of this patent is extended or adjusted under 35 U.S.C. 154(b) by 433 days.

(21) Appl. No.: 16/485,458

(22) PCT Filed: Feb. 14, 2018

(86) PCT No.: PCT/EP2018/053650
§ 371 (c)(1),
(2) Date: Aug. 13, 2019

(87) PCT Pub. No.: WO2018/149863
PCT Pub. Date: Aug. 23, 2018

(65) Prior Publication Data
US 2022/0002712 A1    Jan. 6, 2022

(30) Foreign Application Priority Data

Feb. 14, 2017    (EP) .................................... 17156047

(51) Int. Cl.
*C12N 15/10* (2006.01)
*C08L 53/00* (2006.01)

(52) U.S. Cl.
CPC .......... *C12N 15/1068* (2013.01); *C08L 53/00* (2013.01)

(58) Field of Classification Search
CPC ........................... C12N 15/1068; C08L 53/00
See application file for complete search history.

(56) References Cited

U.S. PATENT DOCUMENTS

2006/0154298 A1    7/2006 Griffiths et al.

FOREIGN PATENT DOCUMENTS

| EP | 3184674 A1 | 6/2017 | | |
|---|---|---|---|---|
| JP | S5529525 A | 3/1980 | | |
| JP | S55144048 A | 11/1980 | | |
| JP | 2002345460 A | 12/2002 | | |
| WO | 2007/048423 A1 | 5/2007 | | |
| WO | WO-2007048423 A1 * | 5/2007 | ............... | C08L 53/00 |
| WO | WO-2013036810 A1 * | 3/2013 | ......... | C12N 15/1093 |
| WO | 2017/108741 A1 | 6/2017 | | |

OTHER PUBLICATIONS

Anderton et al. ("Accelerating Strain-Promoted Azide-Alkyne Cycloaddition Using Micellar Catalysis." Bioconjugate chemistry 26.8 (2015): 1687-1691.). (Year: 2015).*
Anderton 2015 supplementary materials (Year: 2015).*
Duplais et al.( "Organozinc chemistry enabled by micellar catalysis. Palladium-catalyzed cross-couplings between alkyl and aryl bromides in water at room temperature." Organometallics 30.22 (2011): 6090-6097.). (Year: 2011).*
Chen Thesis 1991 (Studies on immobilized polymer-bound imidazole copper (II) complexes as catalysts. Diss. University Library Groningen][Host], 1991.). (Year: 1991).*
Davies, "Organotransition Metal Chemistry: Applications to Organic Synthesis", 1982, pp. 13-17, Pergamon Press.
Giddings, "Use of Multiple Dimensions in Analytical Separations", Multidimensional Chromatography: Techniques and Applications, 1990, p. 1, Marcel Dekker, Inc.
Kabanov et al., "The neuroleptic activity of haloperidol increases after its solubilization in surfactant micelles: Micelles as microcontainers for drug targeting", FEBS Letters, 1989, pp. 343-345, vol. 258, Elsevier Science Publishers B V.
Cotanda et al., "Functionalized Organocatalytic Nanoreactors: Hydrophobic Pockets for Acylation Reactions in Water", Macromolecules, 2012, pp. 2377-2384, vol. 45, No. 5, American Chemical Society.
Moser et al., "Modified Routes to the "Designer" Surfactant PQS", The Journal of Organic Chemistry, 2012, pp. 3143-3148, vol. 77, No. 7, American Chemical Society.
Lu et al., "Micelle-based nanoreactors containing Ru-porphyrin for the epoxidation of terminal olefins in water", Journal of Molecular Catalysis A: Chemical, 2016, pp. 122-125, vol. 417, Elsevier.
Examination Report received for parallel European patent application No. 18 703 801.3 dated Apr. 30, 2021, 6 pages (Reference Purpose Only).
Schönfelder et al., "Amphiphilic Poly(2-Oxazoline)s Bearing Palladium Carbene Complexes for C—C Coupling Reactions in Micellar Catalysis", Polymer Preprints, 2007, pp. 539-540, vol. 48, No. 2.
Office Action received for parallel Japanese patent application No. 2019-565061 dated Nov. 2, 2021, 5 pages, with additional 5 pages of English translation (Reference Purpose Only).
Anderton et al., "Accelerating Strain-Promoted Azide-Alkyne Cycloaddition Using Micellar Catalysis", Bioconjugate Chemistry, 2015, pp. 1687-1691, vol. 26, No. 8.
Duplais et al., "Organozinc Chemistry Enabled by Micellar Catalysis. Palladium-Catalyzed Cross-Couplings between Alkyl and Aryl Bromides in Water at Room Temperature", Organometallics, 2011, pp. 6090-6097, vol. 30, No. 22.
Lipshutz et al., "Micellar Catalysis of Suzuki-Miyaura Cross-Couplings with Heteroaromatics in Water", Organic Letters, 2008, pp. 5329-5332, vol. 10, No. 23.

(Continued)

*Primary Examiner* — Sahana S Kaup
(74) *Attorney, Agent, or Firm* — Viering Jentschura & Partner MBB

(57) ABSTRACT

A method for the synthesis of a chimeric conjugate molecule by micellar catalysis that may form part of DNA-encoded compound libraries. A DNA-coupled organic starter molecule may be reacted with another organic compound, using a catalyst located within a micelle, to form a conjugate of an organic candidate compound coupled to a DNA identifier tag.

16 Claims, 15 Drawing Sheets

(56) References Cited

OTHER PUBLICATIONS

Rosati, "DNA-based catalysis and micellar catalysis", URL: http://www.rug.nl/research/portal/files/14547047/06c6.pdf, 2011, 28 Pages, University of Groningen.
Bingbing et al., "Recent advances on the encoding and selection methods of DNA-encoded chemical library", Bioorganic & Medicinal Chemistry Letters, 2017, pp. 361-369, vol. 27, No. 3.
Sand et al., "Bipyndine-functionalized amphiphilic block copolymers as support materials for the aerobic oxidation of primary alcohols in aqueous media", RSC Advances, 2015, pp. 38235-38242, vol. 5.
Salamon et al., "Chemical Biology Probes from Advanced DNA-encoded Libraries", ACS chemical biology, 2016, pp. 296-307, vol. 11.
Chan et al., "Novel selection methods for DNA-encoded chemical libraries", Current Opinion in Chemical Biology, 2015, pp. 55-61, vol. 26.
Trinh et al., "DNA micelles as nanoreactors: efficient DNA functionalization with hydrophobic organic molecules", ChemComm, 2016, pp. 10914-10917, vol. 52, No. 72.
Extended European search report in parallel EP Patent Application No. 17156047.7 dated May 23, 2017, 8 pages (for reference purposes only).
International search report in parallel PCT Patent Application No. PCT/EP2018/053650 dated Mar. 15, 2018, 10 pages (for reference purposes only).

* cited by examiner

|  | Temp. | conversion to 4 [%][a] | | | | | |
|---|---|---|---|---|---|---|---|
|  |  | 50 eq. 2[b] | | 100 eq. 2[b] | | 500 eq. 2[b] | |
|  |  | 4h | 16h | 4h | 16h | 4h | 16h |
| 100 eq. Cs$_2$CO$_3$[b] | 25°C | n.d. | n.d. | n.d. | n.d. | ~30 | ~50 |
|  | 40°C | ~50 | ~70 | ~90 | ~90 | ~90 | ~90 |
|  | 50°C | ~70 | ~90 | >95[c] | >95[c] | >95[c] | >95[c] |
|  | 60°C | ~90 | 90-95 | >95[c] | >95[c] | >95[c] | >95[c] |
|  | Temp. | 50 eq. 2[b] | | 100 eq. 2[b] | | 500 eq. 2[b] | |
|  |  | 4h | 16h | 4h | 16h | 4h | 16h |
| 200 eq. Cs$_2$CO$_3$[b] | 25°C | n.d. | n.d. | n.d. | n.d. | ~30 | ~50 |
|  | 40°C | ~50 | ~70 | ~85 | ~90 | ~90 | ~90 |
|  | 50°C | ~70 | ~90 | >95[c] | >95[c] | >95[c] | >95[c] |
|  | 60°C | ~90 | >95[c] | >95[c] | >95[c] | >95[c] | >95[c] | a) conversion estimated by MALDI analysis; b) calculated with respect to DNA conjugate 1a; c) no starting material detected.

Figure 8

| Entry | Boronic acid/ester | Conversion to 4a-ag[a] [%] | Entry | Boronic acid/ester | Conversion to 4a-ag[a] [%] |
|---|---|---|---|---|---|
| 2a |  | >95[b] | 2k |  | >95[b] |
| 2b |  | >95[b)d] | 2l |  | ~50 |
| 2c |  | >95[b] | 2m |  | >95[b] |
| 2d |  | >95[b)c] | 2n |  | >95[b] |
| 2e |  | >95[b] | 2o |  | >95[b] |
| 2f |  | >95[b)c)d] | 2p |  | >95[b)d] |
| 2g |  | >95[b)c] | 2q |  | >95[b] |
| 2h |  | >95[b] | 2r |  | >95[b] |
| 2i |  | >95[b)c)d] | 2s |  | >95[b] |
| 2j |  | >95[b)d] | 2t |  | >95[b)d] |

| Entry | Boronic adic/ester | Conversion to 4a-ag[a] [%] | Entry | Boronic adic/ester | Conversion to 4a-ag[a] [%] |
|---|---|---|---|---|---|
| 2u | (HO)₂B-C₆H₄-C(O)CH₃ (3-acetylphenyl) | >95[b] | 2ab | (HO)₂B-CH=CH-(CH₂)₅-CH₃ | ~50[d] |
| 2v | 4-formylphenyl-B(OH)₂ | >95[b] | 2ac | 4-hydroxyphenyl-B(OH)₂ | >95[b] |
| 2w | 4-carboxyphenyl-B(OH)₂ | >95[b] | 2ad | 3,4-dimethoxyphenyl-B(OH)₂ | >95[b] |
| 2x | naphthalen-2-yl-B(OH)₂ | >95[b]c]d] | 2ae | 4-nitrophenyl-B(OH)₂ | >95[b]c] |
| 2y | 2-chlorophenyl-B(OH)₂ | >95[b] | 2af | 4-cyanophenyl-B(OH)₂ | >95[b] |
| 2z | (HO)₂B-C₆H₃(F)(OMe) | >95[b]c] | 2ag | 3-nitrophenyl-B(OH)₂ | >95[b]c] |
| 2aa | 3-(dimethylamino)phenyl-B(OH)₂ | >95[b] | | | | a) Estimated by MALDI-MS; b) no starting material detected; c) reaction with *p*-bromobenzoic acid conjugate 1b; d) boronic acid dissolved in toluene.

Figure 10 continued sequence of 14mer: (NH2) GTC TTG CCG AAT TC mass calc.= 4839; mass found= 4841

METHOD FOR THE SYNTHESIS OF DNA CONJUGATES BY MICELLAR CATALYSIS

CROSS-REFERENCE TO RELATED APPLICATIONS

The present application is a national stage entry according to 35 U.S.C. § 371 of PCT application No.: PCT/EP2018/053650 filed on Feb. 14, 2018; which claims priority to European Patent Application Serial No.: 17156047.7, which was filed on Feb. 14, 2017; both of which are incorporated herein by reference in their entirety and for all purposes.

TECHNICAL FIELD

The present disclosure relates to methods for the synthesis of DNA conjugates that form part of DNA-encoded compound libraries by micellar catalysis using a DNA-coupled organic starter molecule, which is reacted with another organic compound by micellar catalysis to form a conjugate of an organic candidate compound coupled to a DNA identifier tag. The present disclosure further relates to the thus obtained conjugate molecules and the DNA-encoded compound libraries that comprise said conjugates as well as the micelles and aqueous dispersions used in the methods described herein.

BACKGROUND

DNA-encoded chemical libraries (DECLs) represent a tool for drug discovery. DECL technology allows the synthesis and screening of chemical libraries of unprecedented size at moderate costs. DECLs feature the display of individual small organic chemical moieties on DNA fragments serving as amplifiable identification barcodes. The DNA-tag allows the simultaneous screening of a very large set of compounds (up to billions of molecules), because the hit compounds can easily be identified and quantified by PCR-amplification and sequencing of the DNA-barcode. Several approaches have been used to generate DECLs. Most common is the combinatorial mix-and-split synthesis strategy in which preparative organic synthesis and encoding steps are performed in alternated manner.

A prerequisite for the library synthesis is the compatibility of the synthesis methodology used for synthesis of the organic chemical moieties with DNA. Currently, reaction methodology meeting this requirement is very limited. Therefore, DECLs are biased towards a certain chemical space, contradicting the endeavor to design screening libraries to cover chemical space as broad as possible. A current challenge for DECL synthesis research is the development of novel synthetic schemes that furnish in DNA-compatible manner DNA-conjugates of small and geometrically defined (rigid) scaffolds, which serve as starting points for subsequent combinatorial library synthesis.

To overcome the above disadvantages, in the present application micellar catalysis with a catalyst located within the micelle was used for the synthesis of DNA-coupled compounds. The ability to protect DNA from the catalyst, and vice versa the catalyst from poisoning by DNA, during chemical transformations has huge potential. It is well known that the DNA nucleobases have multiple sites for metal co-ordination and hence making it challenging to conduct cross-coupling reactions in the presence of a DNA-tag.

The present inventors found that a chemical reaction can be done on a small organic molecule attached to DNA by micellar catalysis without affecting said DNA. For this purpose, the Suzuki coupling reaction was used as an example to demonstrate feasibility of a catalyst immobilized micellar catalysis. In detail, an NHC-palladium catalyst was used in a micellar catalyzed Suzuki reaction for DNA-encoded chemistry to provide proof-of-concept for micellar catalysis with immobilized catalysts located in the core of the micelles.

SUMMARY

In a first aspect, a method for the synthesis of a chimeric conjugate molecule by micellar catalysis may include:
  forming a reaction mixture comprising
    a conjugate starting molecule comprising a first small organic molecule covalently conjugated to the first DNA identifier tag;
    the second small organic molecule that is to be reacted with the first small organic molecule covalently linked to the first DNA identifier tag to yield the chimeric conjugate molecule;
    an amphiphilic block copolymer comprising a hydrophilic block and a hydrophobic block, wherein the hydrophobic block is functionalized with a catalyst that catalyzes the reaction between the first small organic molecule and the second small organic molecule, wherein the amphiphilic block copolymer is added in an amount that the final concentration of the amphiphilic block copolymer in the reaction mixture is greater than a critical micelle concentration (CMC) of said amphiphilic block copolymer; and
    an aqueous solvent.

The method may further include subjecting the reaction mixture to conditions that allow micelle formation of the amphiphilic block copolymer and to allow formation of the chimeric conjugate molecule from the reaction between the first and second small organic molecule in the interior of the micelle.

The method may further include purifying the chimeric conjugate molecule from the reaction mixture.

In various embodiments, the method further comprises ligating the first DNA identifier tag of the chimeric conjugate molecule to a second DNA identifier tag.

In various other embodiments, the first and/or second DNA identifier tag is at least 4 nucleotides, alternatively at least 5 nucleotides, at least 6 nucleotides, at least 10 nucleotides or at least 14 nucleotides in length.

In still various other embodiments, the first DNA identifier tag is covalently linked to the small organic candidate compound by a linker group, alternatively a poly(ethylene glycol) linker group.

In various embodiments, the first DNA identifier tag or the linker group is covalently linked to the small organic candidate compound by amide bonds.

In further embodiments, the first small organic molecule has a log P (partition coefficient) value above 0.

In various embodiments, the second small organic molecule has a log P (partition coefficient) value above 0.

In various other embodiments, the first small organic molecule is an (hetero)aromatic organic moiety, alternatively an aromatic moiety, such as a phenyl moiety, wherein the (hetero)aromatic moiety is substituted with at least one halogen substituent, such as bromine or iodine. In other alternative non-limiting embodiments, the first organic moiety is a phenyliodide moiety.

In still various other embodiments, the second organic molecules is selected from the group consisting of organic boronic acids or boronic acid esters, alternatively (hetero) aromatic boronic acids or boronic acid esters, alkenes or alkynes.

In various embodiments of the method, the amphiphilic block copolymer comprises poly(styrene-co-N-vinylimidazole) as the hydrophobic block.

In still various embodiments of the method, the amphiphilic block copolymer comprises poly(acrylic acid ester), poly(acrylic acid) or poly(acrylamide).

In various embodiments, the catalyst is a transition metal catalyst, such as palladium, or an acidic group, such as sulfonic acid. In alternative non-limiting embodiments, the catalyst is an N-heterocyclic carbine palladium complex.

In various embodiments, the reaction between the first and second small organic molecule is a Suzuki reaction or a Heck reaction.

In various other embodiments, subjecting the reaction mixture to conditions that allow micelle formation and to allow formation of the chimeric conjugate molecule is carried out at elevated temperature of greater than or equal to 20° C., alternatively ≥40° C., alternatively ≥50° C., or alternatively ≥60° C., but below 95° C. in a non-limiting embodiment.

In still various other embodiments, subjecting the reaction mixture to conditions that allow micelle formation and to allow formation of the chimeric conjugate molecule is carried out for a time period of at least 1, alternatively at least 2, or at least 4 hours.

In various embodiments, the second small organic molecule is used in at least 50 fold, alternatively at least 100 fold molar excess relative to the first small organic molecule.

In further embodiments, purifying the chimeric conjugate molecule from the reaction mixture comprises purifying the chimeric conjugate molecule by chromatography or by precipitation.

In further aspect, a micelle may have an outer hydrophilic portion and an inner hydrophobic portion, comprising (a) a plurality of amphiphilic block copolymer molecules, each comprising a hydrophilic block and a hydrophobic block, wherein the hydrophilic blocks of the plurality of amphiphilic block copolymer molecules form the outer hydrophilic portion of the micelle and the hydrophobic blocks of the plurality of amphiphilic block copolymer molecules form the inner hydrophobic portion of the micelle; and (b) at least one chimeric conjugate molecule comprising a small organic candidate compound inserted into the micelle such that the DNA is predominantly located on the outside of the micelle and the small organic candidate compound is located on the inside of the micelle.

In another aspect, a dispersion composition may include (a) one or more micelle(s) as described herein and (b) a continuous aqueous phase.

In a still further aspect, the chimeric compounds (DNA encoded organic compounds) may be obtainable by the methods described herein.

In still another aspect, a DNA-encoded compounds library may include at least one of the chimeric compounds obtainable by the methods described herein.

It is understood that all combinations of the above disclosed embodiments are also intended to fall within the scope of the claims herein.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the illumination apparatus. In the following description, various aspects are described with reference to the following drawings, in which:

FIG. 8 shows the data concerning the optimization of reaction conditions.

DETAILED DESCRIPTION

Figure 1:
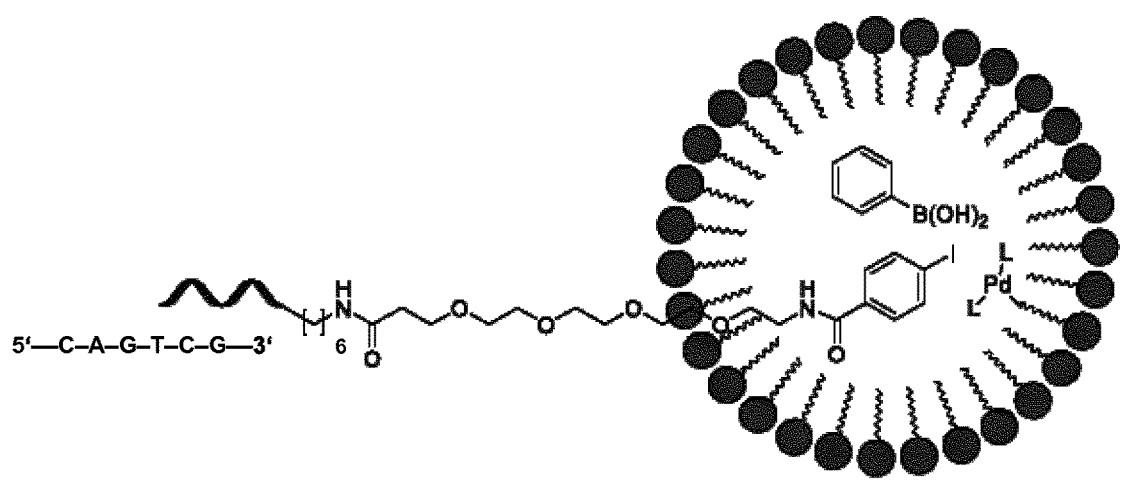
FIG. 1 shows an illustration of the protection of DNA using micellar formation.

The present inventors surprisingly found that two small organic molecules, with one of these molecules being coupled to a DNA tag, can be reacted with each other without affecting the DNA, if said reaction is carried out in a micellar catalysis system. In general, DNA is highly sensitive to chemical alterations induced by a catalyst. The micellar catalysis system allows the spatial separation of DNA and the catalyst and thus protects the chemical stability of the DNA. Therefore, the present method to synthesize compounds broadens the chemical space that can be used for reactions involving educts that are coupled to DNA and may be helpful, for example, to synthesize more diversified DNA-encoded chemical libraries (DECLs).

In a first aspect, a method for the synthesis by micellar catalysis of a chimeric conjugate molecule comprises
  (A) a small organic candidate compound, wherein said small organic candidate compound is obtainable by reacting a first small organic molecule with a second small organic molecule, covalently conjugated to
  (B) a first DNA identifier tag,
  wherein said method comprises
  (a) combining in an aqueous solvent
    (1) a conjugate starting molecule comprising the first small organic molecule covalently conjugated to the first DNA identifier tag;
    (2) the second small organic molecule that is to be reacted with the first small organic molecule covalently linked to the first DNA identifier tag to yield the chimeric conjugate molecule; and
    (3) an amphiphilic block copolymer comprising a hydrophilic block and a hydrophobic block, wherein the hydrophobic block is functionalized with a catalyst that catalyzes the reaction between the first and second small organic molecule, to yield a reaction mixture with the aqueous solvent as the continuous phase, wherein the amphiphilic block copolymer is added in an amount that the final concentration of the amphiphilic block copolymer in the reaction mixture is above the critical micelle concentration (CMC) of said amphiphilic block copolymer;

(b) subjecting the reaction mixture to conditions that allow micelle formation of the amphiphilic block copolymer and the reaction between the first and second small organic molecule in the interior of the micelle; and (c) purifying the chimeric conjugate molecule from the reaction mixture.

The term "micellar catalysis", as used herein, relates to a chemical reaction in solution by the addition of an amphiphile capable of forming micelles, here the amphiphilic block copolymer, at a concentration higher than its critical micelle concentration so that micelles form and the reaction can occur in the environment of said micelles. Without wishing to be bound to a specific theory, it is believed that the occurrence of said reaction may be due, for example, to higher concentration of the reactants in the micelle, more favorable orientation and solvation of the species, or enhanced rate constants in the micellar pseudo phase of the surfactant aggregate.

The term "chimeric conjugate molecule", as used herein, refers to a compound comprising two or more types of molecules that are chemically linked to each other, typically by a covalent bond. The chimeric conjugate compounds comprise a small organic candidate compound covalently coupled to a nucleic acid, such as DNA, moiety. The nucleic acid may be single- or double-stranded, such as single- or double-stranded DNA, alternatively double-stranded DNA. Also encompassed are DNA derivatives that are modified to increase stability. The type of covalent bond may vary depending on the desired linking chemistry. Suitable chemical bonds are well known in the art and include, without limitation, amide bonds, disulfide bonds, thioester bonds, triazole bonds, and ester bonds. The DNA may be modified with an amino group, in a non-limiting embodiment, which is then reacted with an amino-reactive group on the organic molecule, such as a carboxyl group. The nucleic acid moiety and the organic molecule may be linked by amide bond.

The term "small organic candidate compound" refers to carbon-based compounds, in particular small organic molecules. The organic candidate compounds may display biological activity such as, but not limited to pharmaceutical, antibiotic, pesticidical, herbicidical, or fungicidical activity. The organic candidate compound may include a (hetero)cyclic structure, such as an aromatic alicyclic ring or ring system or a respective heteroaryl or heterocyclic structure.

The term "(hetero)cyclic," as used herein, means an aromatic or non-aromatic saturated mono- or multi-, such as bi- or tricyclic, ring system, including annealed and condensed ring systems, having 2 to 20, such as 2 to 14 ring carbon atoms, and optionally containing 1-5 ring atoms chosen from O, S, and N. Non-limiting examples of suitable heterocyclic ring systems include furanyl, imidazolyl, isoxazolyl, oxadiazolyl, oxazolyl, pyrazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, or benzoisoxazolyl. Non-limiting examples of suitable heterocyclic rings include also aziridinyl, piperidinyl, pyrrolidinyl, piperazinyl, tetrahydropyranyl, tetrahydrofuranyl, tetrahydrothiophenyl, morpholinyl, thiomorpholinyl and the like. The small organic candidate compound is generally obtainable by reacting a first small organic molecule with a second small organic molecule. In one embodiment, the small organic candidate compound can be selected from the group comprising small molecules conforming or not conforming to Lipinski's rule of five, (cyclic) peptides, mixtures thereof.

The "organic molecule", as used herein, may refer to molecules of different classes such as small molecules conforming or not conforming to Lipinski's rule of five.

"Small" in the context of the term "first and/or second organic molecule", as used herein, relates to compounds that consist of 2 or more carbon atoms and up to 50 carbon atoms, alternatively up to 30, up to 29, up to 28, up to 27, up to 26, up to 25, up to 24, up to 23, up to 22, up to 21, up to 20, up to 19, up to 18, up to 17, up to 16 or up to 15 carbon atoms. In other various embodiments, a "small" organic molecule has a molecular weight of at most 1500 daltons, alternatively at most 700 daltons, or at most 500 daltons in a non-limiting embodiment.

In still further embodiments, the first and/or the second small organic molecule has a log P (partition coefficient) value above 0. The first small organic molecule may have a log P value above 0, such as more than 0.5, more than 1.0, more than 2.0 or more than 3.0. The log P value is as defined below.

The first and the second small organic molecule are selected such that by reacting with each other the desired candidate compound is formed. To achieve this both molecules may be selected from organic moieties, as defined above that comprise functional groups that allow the desired reaction to occur. Such groups include, without limitation, halogen, hydroxyl, carboxyl, carbonyl, amine, sulfonate, phosphonate, and the like and also combinations of the afore-mentioned such as amide groups, but also groups with carbon double and triple bonds, such as vinyl, allyl and alkenyl groups. The backbone structure of the compound may be an alkane, cycloalkane, aryl or the respective hetero variant thereof.

In various embodiments, the small organic molecules may thus be selected from the group consisting of a linear or branched, substituted or unsubstituted alkyl, linear or branched, substituted or unsubstituted heteroalkyl, linear or branched, substituted or unsubstituted alkenyl, linear or branched, substituted or unsubstituted heteroalkenyl, linear or branched, substituted or unsubstituted alkynyl, linear or branched, substituted or unsubstituted heteroalkynyl, substituted or unsubstituted cycloalkyl, substituted or unsubstituted heterocycloalkyl, substituted or unsubstituted aryl, or substituted or unsubstituted heteroaryl, linear or branched, substituted or unsubstituted alkylaryl, linear or branched, substituted or unsubstituted heteroalkylaryl, each having up to 20 carbon atoms.

The term "alkyl", by itself or as part of another substituent, means, unless otherwise stated, a straight (i.e. unbranched) or branched chain, or combination thereof, which is be fully saturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like.

The term "alkylene", by itself or as part of another substituent, means a divalent radical derived from an alkyl, as exemplified, but not limited, by —$CH_2CH_2CH_2CH_2$—.

Typically, an alkyl (or alkylene) group will have from 1 to 24 carbon atoms, with those groups having 10 or fewer carbon atoms being preferred. A "lower alkyl" or "lower alkylene" is a shorter chain alkyl or alkylene group, generally having eight or fewer carbon atoms.

The term "heteroalkyl", by itself or in combination with another term, means, unless otherwise stated, a stable straight or branched chain, or cyclic hydrocarbon radical, or combinations thereof, consisting of at least one carbon atom and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, $CH_2$—$CH_2$, —S(O)—$CH_3$, —$CH_2$—$CH_2$—S(O)$_2$—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O$_2$)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (such as from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from an aryl and heteroaryl, respectively.

The term "arylalkyl" is meant to include those radicals in which an aryl group is attached to an alkyl group (e.g., benzyl, phenethyl, pyridylmethyl and the like). The term "heteroarylalkyl" includes the above described groups, wherein one or more carbon atoms of the alkyl or aryl portion (e.g., a methylene group) are replaced by, for example, an oxygen atom (e.g., phenoxymethyl, 2-pyridyloxymethyl, 3-(1-naphthyloxy)propyl, and the like).

Where a heteroalkyl, heterocycloalkyl, or heteroaryl includes a specific number of members (e.g. "3 to 7 membered"), the term "member" refers to a carbon or heteroatom.

Each of the above terms (e.g., "alkyl," "heteroalkyl," "aryl" and "heteroaryl") are meant to include both substituted and unsubstituted forms of the indicated radical. Non-limiting substituents for each type of radical are provided below.

Substituents for the alkyl, heteroalkyl, alkylene, alkenyl, heteroalkylene, heteroalkenyl, alkynyl, cycloalkyl, heterocycloalkyl, cycloalkenyl, and heterocycloalkenyl radicals can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound includes more than one R group, each of the R groups is independently selected. The same applies to R', R", R''' and R"" groups when more than one of these groups is present. When R' and R" are attached to the same nitrogen atom, they can combine with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: halogen, —OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxy, and fluoro ($C_1$-$C_4$)alkyl, in a number ranging from zero to the total number of open valences on the aromatic ring system; and where R', R", R''' and R"" are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound includes more than one R group, each of the R groups is independently selected. The same applies to R', R", R''' and R"" groups when more than one of these groups is present.

The term "alkene", as used herein, denotes molecules composed solely of carbon and hydrogen, containing one carbon-carbon double bond and having the chemical formula of a mono-unsaturated hydrocarbon, $C_nH_{2n}$, where n equals at least two. In a non-limiting embodiment, n equals at least 3, 4, 5 or 6. Alternatively, n is at most 6.

The first small organic molecule may be selected such that it has the desired hydrophobicity to ensure its location on the inside of the micelle, such as hydrophobic structural elements, such as alkyl and aryl groups and substituents such as halogen. For the Suzuki and Heck reaction, the first small organic molecule is a halogen-substituted aryl moiety, such as phenyl.

The term "DNA identifier tag", as used herein, refers to a DNA sequence that is covalently coupled to a small organic candidate compound, as defined above, to form a chimeric conjugate molecule. The terms "nucleotide", "nucleic acid molecule" or "nucleic acid sequence", as interchangeably used herein, relate to DNA (deoxyribonucleic acid) molecules, RNA (ribonucleic acid) molecules or molecules comprising both, DNA and RNA, e.g. DNA. In certain embodiments, derivatives of DNA or RNA or modified variants thereof may also be used. Such derivatives may include structural elements that increase the stability of the nucleic acid. Said molecules may appear independent of their natural genetic context and/or background. The term "nucleic acid molecule/sequence" further refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term "nucleic acid molecule", and in particular "DNA" or "RNA" molecule, refers only to the primary and secondary structure of the molecule, and does not limit it to any particular tertiary forms. The first and/or the second DNA identifier tag may include natural and/or non-natural bases as described below. The DNA identifier tag may be double or single stranded. In non-limiting embodiments, the DNA identifier tag is double stranded. The DNA identifier tag is covalently conjugated to the small organic candidate compound or to the linker group to form the chimeric conjugate molecule. The small organic candidate compound or to the linker group can be attached to the 3'-end or the 5'-end of the DNA identifier tag. In non-limiting embodiments, the small organic candidate compound or to the linker group are attached to the 5'-end of the DNA identifier tag.

"DNA" or "deoxyribonucleic acid", as interchangeably used herein, relates to a chain of nucleotides, wherein the nucleotides contain the sugar 2'-deoxyribose and bases selected from adenine (A), guanine (G), cytosine (C) and thymine (T).

The term "base" or "nucleobase", as interchangeably used herein, relates to nitrogen-containing biological compounds (nitrogenous bases) found linked to a sugar within nucleosides—the basic building blocks of deoxyribonucleic acid (DNA) and ribonucleic acid (RNA). Their ability to form base pairs and to stack upon one another lead directly to the helical structure of DNA and RNA. The primary, or canonical, nucleobases are cytosine (DNA and RNA), guanine (DNA and RNA), adenine (DNA and RNA), thymine (DNA) and uracil (RNA), abbreviated as C, G, A, T, and U, respectively. Because A, G, C, and T appear in the DNA, these molecules are called DNA-bases; A, G, C, and U are called RNA-bases. Uracil and thymine are identical except that uracil lacks the 5' methyl group. Adenine and guanine belong to the double-ringed class of molecules called purines (abbreviated as R). Cytosine, thymine, and uracil are all pyrimidines (abbreviated as Y). Other bases that do not function as normal parts of the genetic code are termed non-canonical. Nucleobases that can be included in the first and/or second DNA identifier tag are thymine, cytosine, uracil, 4-acetylcytidine, 5-(carboxyhydroxymethyl)uridine, 2'-O-methylcytidine, 5-carboxymethylaminomethyl-2-thiouridine, 5-carboxymethylaminomethyluridine, dihydrouridine, 2-O-methylpseudouridine, 1-methylpseudouridine, 3-methylcytidine, 5-methylcytidine, 5-methylaminomethyluridine, 5-methoxyaminomethyl-2-thiouridine, 5-methoxycarbonylmethyl-2-thiouridine, 5-methoxycarbonylmethyluridine, 5-methoxyuridine, uridine-5-oxyacetic acid-methylester, uridine-5-oxyacetic acid, pseudouridine, 2-thiocytidine, 5-methyl-2-thiouridine, 2-thiouridine, 4-thiouridine, 5-methyluridine, 2'-O-alkyluridine, 2'-O-alkylthymidine, 2'-O-alkylcytidine and 3-(3-amino-3-carboxypropyl)uridine.

The first small organic molecule used herein for micellar catalysis is connected to a single- or double-stranded DNA sequence modified by any commercially available DNA modifier. These modifiers are commercially available, for example, by Glen Research or Iba-Lifesciences. The DNA identifier tag may be coupled to a modifier at the 5'-end, at the 3'-end, or at any internal nucleotide of the DNA identifier tag. The modifiers may be introduced into DNA sequences by the phosphoramidite method. They contain a reactive group such as an amine, carboxylic acid, thiol, halide, maleimide, aminooxy, aldehyde, or terminal alkyne. Reactants, namely the first small organic molecules, are coupled to these modifiers by amide bond formation, (thio)urea synthesis, alkylation, Diels-Alder reaction, hydrazine formation, and azide-alkyne cycloaddition to yield the conjugate starting molecule.

Examples of commercially available modifiers are the terminal modifiers 5'-amino-C(6)-phosphate linker, 3'-amino-C(7)-phosphate linker, and the internal modifier amino-C6 dT. In non-limiting embodiments, the modifier is a linear or branched alkyl group having 1 to 20 carbon atoms that contains on its non-conjugated end an amine group and that is coupled to the 5'-phosphate, 3'-phosphate or 2'-phosphate of a terminal or internal nucleotide, such as the terminal nucleotides.

By the term "aqueous", as used herein, is meant that the solvent used in the composition is predominantly water, i.e. comprises at least 50 vol. % water. Hence, "aqueous" and "water-based" may be considered synonyms. The term "aqueous solvent", as used herein, refers to water, such as distilled water, deionized water, sterile water, a buffer or a salt solution with water as the main solvent. The aqueous solvent optionally includes one or more dissolved additives and/or excipients, in particular organic co-solvents that are miscible with water and do not adversely affect the micelle formation. In non-limiting embodiments, the aqueous solvent comprises at least 50%, at least 60%, at least 70%, at least 80%, at least 90%, at least 95% or at least 99% water (vol. %).

The term "conjugate starting molecule", as used herein, refers to a molecule comprising the first small organic molecule covalently conjugated to the first DNA identifier tag, wherein the first small organic molecule and the DNA identifier tag are defined as described above. Examples for conjugate starting molecules are disclosed, for example, in the international patent publication WO 2017/108741 A1 throughout the whole application, which is hereby incorporated by reference in its entirety. In more detail, suitable conjugate starting molecules are described on page 7, last paragraph to page 9, first paragraph, of said application.

"Reacted", as used herein, refers to a chemical reaction between the first small organic molecule covalently linked to the first DNA identifier tag and the second small organic molecule to result in chimeric conjugate molecule. Said reaction is catalyzed by a catalyst as described below and occurs in a micelle. The reaction may include, without further limitation, synthesis reaction, decomposition reaction, single replacement reaction or double replacement reaction, such as oxidation and reduction reaction, complexation reaction, acid-base reaction, precipitation reaction, solid-state reaction or photochemical reaction.

The term "block copolymer", as used herein, refers to a copolymer comprising two or more different types of monomeric subunits, wherein the monomeric subunits are grouped into blocks containing only one type of monomeric subunit. These blocks are covalently attached to other blocks containing different subunits in the same polymer chain, and the monomeric subunits of the block copolymer undergo phase-segregated arrangement as a result of the affinity of the monomeric subunits to organize with similar monomeric subunits, for example, by forming a micelle. The amphiphilic block copolymer of the present application comprises a hydrophilic block and a hydrophobic block. In non-limiting embodiments, the amphiphilic block copolymer is a diblock copolymer. The term "diblock copolymer", as used herein, refers to a block copolymer in which there are only two different types of blocks (here a hydrophobic and hydrophilic block) each having a different type of monomeric subunits. The term "amphiphilic", as used herein, describes a three-dimensional structure having discrete hydrophobic and hydrophilic regions. An amphiphilic polymer requires the presence of both hydrophobic and hydrophilic elements along the polymer backbone.

The hydrophobic and the hydrophilic block of the amphiphilic block copolymer comprise monomeric subunits, wherein the hydrophilic block comprises at least 70%, at least 80%, at least 90% or at least 95% or consists of hydrophilic monomer subunits and the hydrophobic block comprises at least 70%, at least 80%, at least 90% or at least 95% or consists of hydrophobic monomer subunits. In non-limiting embodiments, the hydrophobic and/or hydrophilic block each comprise at least 10 monomeric subunits, alternatively at least 20, at least 30, at least 40 or least 50 monomeric subunits.

To form the respective polymer blocks, monomeric subunits of the respective type are polymerized.

The term "hydrophilic" or "hydrophilic block", as used herein, is descriptive of or denoting a part of the copolymer having an affinity for water. In non-limiting embodiments, "hydrophilic", as used herein in connection to monomeric units, refers to a molecule that has a log P of less than 1.0, such as less than 0.75, less than 0.5, less than 0.25 or less than 0.1.

In non-limiting embodiments, the monomeric subunits of the hydrophilic block are selected from the group consisting of hydrophilic alkylene oxides, such as ethylene oxide, (meth)acryl amide and hydrophilic derivatives thereof, such as N-(short chain)alkyl/heteroaryl and N,N-(short chain) dialkyl/heteroaryl derivatives thereof, with the respective alkyl/heteroaryl group optionally substituted, for example with functional groups, such as hydroxyl (concrete examples include, but are not limited to N-methylacrylamide, N,N-dimethylacrylamide, N-isopropylacrylamide, N-acryloylmorpholine, N-(2-hydroxypropyl)methacrylamide, N-acryloylpyrrolidine, N-vinylpyrrolidone); quaternary ammonium based polymers, based on ethylenically unsaturated ammonium monomers, such as diallyldimethylammonium chloride; (meth)acrylic acid and hydrophilic esters thereof, such as those with ethylene oxide units or with sulfonated or carboxylated alkyl groups, such as 2-(2-ethoxyethoxy)ethyl acrylate, acrylic acid methylester methoxyethylene, poly ethoxy (10) ethyl methacrylate, 2-sulfoethyl methacrylate, 3-sulfopropyl acrylate, 3-sulfopropyl methacrylate; amino acids, such as aspartic acid, glutamic acid, L-lysine; vinyl alcohol, vinyl acetate and hydrophilic vinyl and allyl ethers, such as 2-ethoxyethyl vinyl ether, 2-methoxyethyl vinyl ether, methyl tri(ethyleneglycol) vinyl ether, methyl vinyl ether, sodium 1-allyloxy-2-hydroxypropyl sulfonate; oxazolines and derivatives thereof, such as 2-alkylsubstituted 2-oxazolines, such as 2-methyl-2-oxazoline, 2-ethyl-2-oxazoline; ethylene imine; and hydrophilic styrenes, such as those based on styrene carboxylate/sulfonates.

Accordingly, the hydrophilic block may comprise polyoxyalkylenes, (poly)acrylic acid or hydrophilic esters or amides thereof, vinyl alcohols and the like. Also possible are, for example, (poly)lactic acid, (poly)glycolic acid or copolymers thereof.

In non-limiting embodiments, the below described monomeric subunits are polymerized to form the hydrophobic block of the amphiphilic block copolymer.

The term "hydrophobic" or "hydrophobic block", as used herein, is descriptive of or denoting a part of the copolymer having a lack of affinity for water.

In non-limiting embodiments, "hydrophobic", as used herein in connection to monomeric units, refers to a molecule or portion of a molecule that has a log P of at least 1.0, such as at least 1.5, at least 2.0, at least 2.5 or at least 3.0.

In non-limiting embodiments, the hydrophobic monomeric subunits of the hydrophobic block or the respective polymers are selected from the group consisting of (poly) styrene and hydrophobic derivatives thereof, such as alkyl-styrenes, such as tert-butylstyrene, styrene-co-[p-(2,2,2-trifluoro-1-hydroxy-1-trifluoromethyl)ethylmethylstyrene; polyolefines, such as polypropylene, ethylene-co-butylene, isobutylene; polyoxyalkylenes with monomers with 3 and more C atoms, such as propylene oxide, butylene oxide; 2-R 2-oxazoline (R=alkyl with more than 2 C-atoms); (meth) acrylates with alkyl moieties and aryl moieties and C6+ heteroalkyl moieties (alkyl moieties of 6 or more carbon atoms comprising 1 or more heteroatoms in the alkyl chain), such as t-butyl (meth)acrylate, n-butyl (meth)acrylate, isobutyl (meth)acrylate, sec-butyl (meth)acrylate, cyclohexyl (meth)acrylate, iso-decyl(meth)acrylate, n-dodecyl (meth) acrylate, N(n-dodecyl)methacrylamid, 2-ethylhexyl (meth) acrylate, 1-hexadecyl (meth)acrylate, n-hexyl (meth)acrylate, 2-naphthyl (meth)acrylate, n-octyl (meth)acrylate, 2-phenoxyethyl (meth)acrylate, stearyl (meth)acrylate (mixture of C16/C18), tert-butylaminoethyl(meth)acrylate, N,N-diisopropylaminoethyl (meth)acrylate, N,N-diethylaminoethyl (meth)acrylate, N,N-dimethylaminoethyl (meth) acrylate, cinnamoylethyl (meth)acrylate, t-amyl (meth) acrylate, benzyl (meth)acrylate, triethylene glycol monomethyl ether mono(meth)acrylate, undecyl (meth) acrylate, methyl(meth)acrylate, 2-(N-morpholinoethyl) (meth)acrylate, 1,1,2,2-tetrahydroperfluorooctyl acrylate; diene-based polymers, such as those based on butadiene, isoprene, N,N-dimethylaminoisoprene; γ-benzyl-L-glutamate; ε-caprolactone; siloxanes, such as dimethylsiloxane methylphenylsilane; hydrophobic acrylamides, such as long-chained (C6+) alkyl acrylamides, such as N-(n-Octadecyl)acrylamide, N-isopropyl acrylamide, vinylpyridine, 2-vinylpyridine, 3-vinylpyridine, 4-vinylpyridine, acrylonitrile; isocyanate-based monomers, such as hexyl isocyanate and isocyanodipeptide.

Non-limiting hydrophobic blocks comprise polystyrene, hydrophobic polyacrylates and polyacrylamides.

In various embodiments, the amphiphilic block copolymer is a combination consisting of at least one of the above described hydrophobic blocks and at least one of the above described hydrophilic blocks.

"Catalyst", as used herein, refers to a chemical agent that facilitates a chemical method or process. In one embodiment, the term refers to a substance that initiates or accelerates a chemical reaction without itself being affected. Catalysts facilitate the chemical reactions between hydrocarbons, oxidants, solvents and other components of a chemical transformation.

In non-limiting embodiments, the catalyst may be selected from the group consisting of an organo-catalyst, a (transition) metal catalyst or metal-nanoparticle(s). The term "organo-catalyst", as used herein, includes organic molecules capable of catalyzing a reaction. In non-limiting embodiments, the organo-catalyst comprises an organic acid or an organic base.

In non-limiting embodiments, the organo-catalyst is selected from the group consisting of alkane sulfonic acids, benzene sulfonic acids, carboxylic acids, tertiary amines, secondary amines, e.g. proline derivatives, thioureas and imidazolinones. The organo-catalyst can be coupled to the hydrophobic block by suitable chemical bonds that are well known in the art, such as amide bonds, disulfide bonds, thioester bonds, and ester bonds. In non-limiting embodiments, the organo-catalyst may relate to a compound that consists of 2 or more carbon atoms, such as up to 50 carbon atoms, alternatively up to 30, up to 29, up to 28, up to 27, up to 26, up to 25, up to 24, up to 23, up to 22, up to 21, up to 20, up to 19, up to 18, up to 17, up to 16 or up to 15 carbon atoms. In other various embodiments, the organic molecule has a molecular weight of at most 1500 daltons, such as at most 700 daltons, or alternatively at most 500 daltons.

The term "transition metal catalyst", as used herein, means any transition metal useful in reacting the first and second small organic molecule including salts, carbonyl compounds, chelates, or complexes with ligands having trivalent donor groups of the metals in Group VIII or copper. A Group VIII metal includes Fe, Co, Ni, Ru, Rh, Pd, Os, Ir, or Pt. Complex catalysts are those with ligands having trivalent donor atoms and are comprised of a Group VIII metal complexed by one or more ligands. These complexes are formed by the reaction of a Group VIII metal compound and a ligand having a trivalent donor atom. Such trivalent donor atoms include phosphorus, nitrogen, arsenic, antimony and bismuth. These types of complexes are well known to those of ordinary skill in the art and most commonly involve phosphorus-type ligands. (see R. F. Heck, Palladium Reagents in Organic Syntheses, Academic Press, N.Y., N.Y., 1985, pages 1-7; S. G. Davies, Organotransition Metal Chemistry Applications to Organic Syntheses, Pergamon Press, N.Y., N.Y., 1985, pages 13-17). Examples of the most common phosphorus-type ligands include phosphines such as triphenylphosphine, trimethylphosphine, methyldiphenylphosphine, dimethylphenylphosphine, dicyclohexylphenylphosphine, diphenylenephenylphosphine, tri-p-tolylphosphine, tri-(p-chlorophenyl)phosphine, tris(p-methoxyphenyl)phosphine, bis-(diphenylphosphino) methane, 1,2-bis-(diphenylphosphino)ethane, bis-(dicyclohexylphosphino)ethane, bis-(2-diphenylphosphinoethyl)phenylphosphine, 1,1,1-tris-(diphenylphosphinomethyl)ethane, tris-(2-diphenylphosphinoethyl)phosphine, 1,1,4,7,10,10-hexaphenyl-1,4,7,10-tetraphosphadecane, and 1,1-bis-(diphenylphosphino)ferrocene. The complex catalysts are used in conjunction with a ligand having a trivalent donor atom. The ligand is phosphine or a phosphine derivative such as those listed above. The relative amounts of phosphine and Group VIII metal, which can be used in the method are best expressed as a ratio of the number of moles of phosphorus in the phosphine compound to the number of moles of Group VIII metal. The catalysts are salts, carbonyl compounds, chelates, or complexes of Rh, Pd, Ir, and Ru. Non-limiting catalysts are $RhCl_3$, $PdCl_2$, $PdBr_2$, $IrCl_3$, $Pd(OOCCH_3)_2$, $(RhCl(CO)_2)_2$, palladium bis triphenylphosphine, palladium tris triphenyl phosphine, and $Pd(OAc)_2$.

In other non-limiting embodiments, the metal (ion) catalysts and ligands used to connect the metal (ion) catalyst to the lipophilic block of the amphiphilic block copolymer are any combination of the catalysts and ligands as described below. The metal (ion) catalyst may be selected from the group consisting of Pd(O), Pd(II), Co(II), Au(I), Ag(I), Cu(I), Cu(II), Ru(II), Rh(III), Co(III) and Yb(III). The ligand may be selected from the group consisting of N-heterocyclic carbenes, phosphine derivatives, phosphine/nitrogen derivatives, salene derivatives, pyridine and bipyridine derivatives, 1,3-oxazolidine derivatives, pyrazinyl derivatives, camphor derivatives and oxazoline derivatives.

Non-limiting metal nanoparticles catalyzing the reaction between the first and the second small organic molecule are metal nanoparticles based on palladium, platinum, gold, copper, ruthenium, rhodium, iron, cobalt as metal component and N heterocyclic carbene ligand derivatives or phosphine ligand derivatives. The term "nanoparticle", as used herein, indicates a composite structure of nanoscale dimensions. In particular, nanoparticles are typically particles of a size in the range of from about 1 to about 1000 nm, and are usually spherical although different morphologies are possible depending on the nanoparticle composition. The portion of the nanoparticle contacting an environment external to the nanoparticle is generally identified as the surface of the nanoparticle. In nanoparticles herein described, the size limitation can be restricted to two dimensions and so that nanoparticles herein described include composite structure having a diameter from about 1 to about 1000 nm, where the specific diameter depends on the nanoparticle composition and on the intended use of the nanoparticle according to the experimental design. For example, nanoparticles to be used in applications typically have a size of about 200 nm or below, in particular ranging from about 1 to about 100 nm.

"Functionalized," as used herein in the context of the catalyst and the hydrophobic block, means that the hydrophobic block comprises the catalyst in that the catalyst is bound to the hydrophobic block of the polymer. This ensures that the catalyst is localized on the inside of the micelle. Examples of the hydrophobic block and the catalyst are provided above. In non-limiting embodiments, the hydrophobic polymer block is covalently bound to (a) the organocatalyst, (b) a ligand complexing the transitions metal catalyst or (c) a functional group that coordinates metal-nanoparticles that function as a catalyst.

As used herein, "continuous phase" refers to the phase external to the dispersed discontinuous phase in an emulsion or dispersion. The continuous phase is formed by the aqueous solvent, while the dispersed phase comprises the micelles.

As used herein, "critical micelle concentration" or "CMC" refers to the concentration of the amphiphilic block copolymer, at which additional copolymer substantially forms micelles. Typically, there is a relatively small range of concentrations separating the limit below which substantially no micelles are detected and the limit above which substantially all additional copolymer molecules form micelles. Many properties of surfactant solutions (the copolymer may be assumed to represent a surfactant here), if plotted against the concentration, appear to change at a different rate above and below this range. By extrapolating the loci of such a property above and below this range until they intersect, a value can be obtained known as the critical micellization concentration or critical micelle concentration (CMC). The CMC value can also be viewed as the concentration at which surface tension stabilizes. Further, the CMC value for a surfactant can depend on the liquid solvent. Thus, the CMC value of a surfactant can vary from that typically found in pure water. The methods to determine the CMC are well-known in the art. Other parameters than the surfactant concentration that may influence the formation of micelles are, but not limited to the solvent, temperature, atmosphere pressure etc. All these parameters form the "conditions that allow micelle formation", whereas the concentration of the surfactant (namely the CMC) may be most critical and influential. In some embodiments, the conjugate starting molecule and/or the second small organic molecule are dissolved in an organic solvent, such as toluene, before they are combined with the other components to form a micelle.

The term "purifying", as used herein, refers to increasing the degree of purity of the chimeric conjugate molecule in the reaction mixture by removing one or more contaminants, e.g., non-reacted educts or intermediate compounds, from the reaction mixture. "Removal" of the contaminant may not be a complete removal. A "purified" chimeric conjugate molecule, in accordance with the application is typically at least 70%, such as at least 80%, at least 85%, at least 90%, at least 95% or at least 99% by weight of the remaining reaction mixture after purification.

In non-limiting embodiments, the catalyst (and the first and second small organic molecule) are selected from the group of catalysts (and first and second small organic molecules) as indicated in Table 1 to catalyze the indicated reaction:

TABLE 1

Exemplary reactions catalysed by micellar catalysis

| catalyst | Reaction (educts correspond to the conjugate starting molecule and the second small organic molecule; products correspond to the chimeric conjugate molecule) |
|---|---|
| Pd(O) | Suzuki reaction, Heck reaction 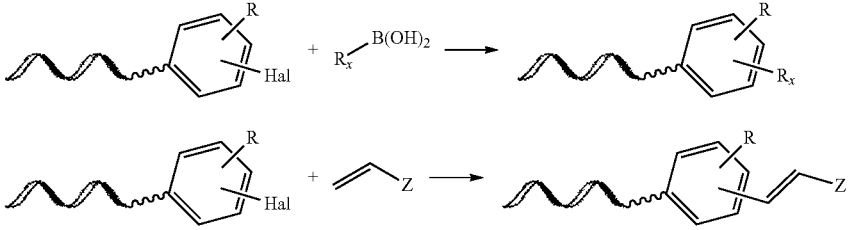 |
| Pd(II) | Suzuki reaction, Heck reaction 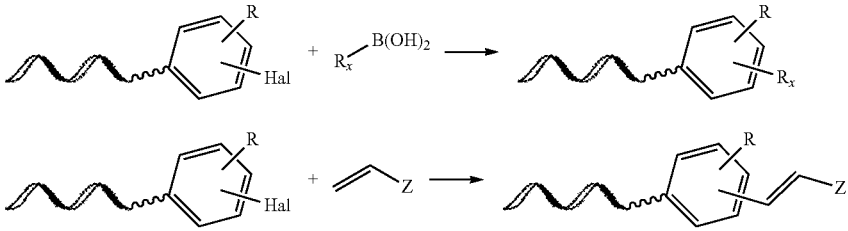 |

TABLE 1-continued

Exemplary reactions catalysed by micellar catalysis

| catalyst | Reaction (educts correspond to the conjugate starting molecule and the second small organic molecule; products correspond to the chimeric conjugate molecule) |
|---|---|
| Au(I) | alkyne-aldehyde-amine three component reaction (PCT/EP2016/081845) |
| Ag(I) | 3 + 2 cycloaddition of azomethine ylides with dipolarophiles (PCT/EP2016/081845) |
| Cu(I) | 3 + 2 cycloaddition of azomethine ylides with dipolarophiles (PCT/EP2016/081845) |
| Cu(II) | oxidation of alcohols to aldehydes (H. Sand, R. Weberskirch, RSC Adv. 2015, 5, 38235-38242.) |

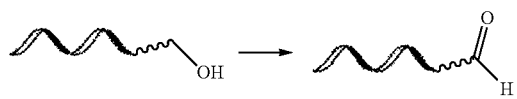

| Ru(II) | ring-closing metathesis (PCT/EP2016/081845), metathesis |

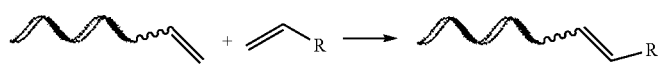

| Rh(III) | cyclization cascade (B. Rossbach, K. Leopold, R. Weberskirch, Angew. Chem Int. Ed. 2006, 45, 1309-1312) |

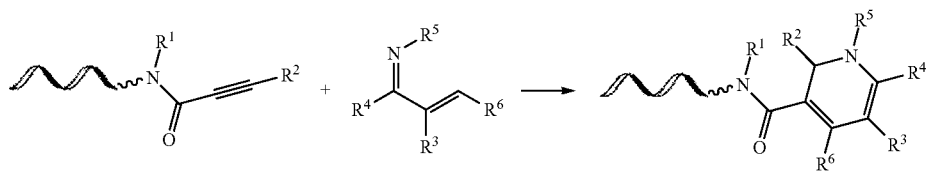

| Co(II) | Kinetic racemate resolution of epoxides |

| Co(III) | Cobalt(III)-Catalyzed Synthesis of Indazoles by C—H Bond Functionalization/Addition/Cyclization Cascades (T. Mesganaw, J. A. Ellman, Org. Process Res. Dev., 2014, 18 (9), pp 1097-1104) |

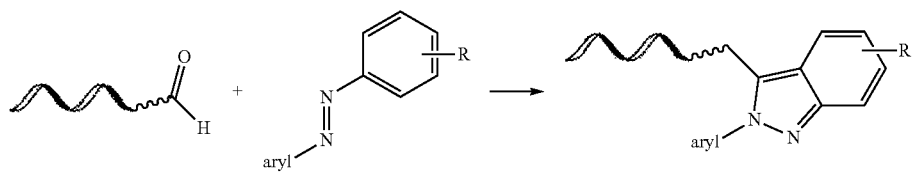

| Yb(III) | Diels-Alder reactions (J. R. Hummel, J. A. Ellman, J Am Chem Soc. 2015 Jan 14; 137(1), 490-498.) |

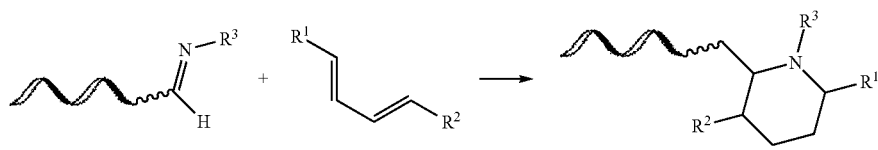

| alkane sulfonic acids | Boc-deprotection, Pictet-Spengler reaction (PCT/EP2016/081845) |
| benzene sulfonic acids | Boc-deprotection, Pictet-Spengler reaction (PCT/EP2016/081845) |

TABLE 1-continued

Exemplary reactions catalysed by micellar catalysis

| catalyst | Reaction (educts correspond to the conjugate starting molecule and the second small organic molecule; products correspond to the chimeric conjugate molecule) |
|---|---|
| tertiary amines | aldol reactions 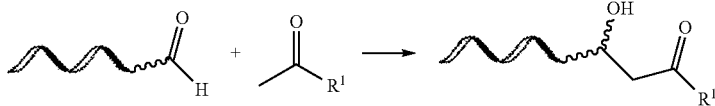 |
| secondary amines | aldol reactions 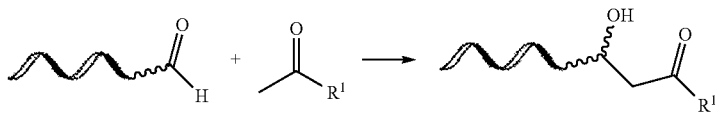 |
| thioureas | Diels-Alder reactions (K. Cheng, L. Lin, S. Chen, X. Feng, Tetrahedron, 2005, 61, 9594-9599) 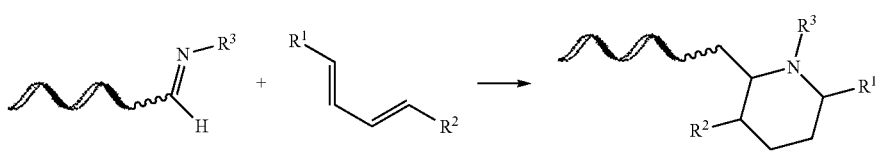 | wherein "〜〜〜" is a linker group selected from the group consisting of nothing, a linear or branched, substituted or unsubstituted alkyl, linear or branched, substituted or unsubstituted heteroalkyl, linear or branched, substituted or unsubstituted alkenyl, linear or branched, substituted or unsubstituted heteroalkenyl, linear or branched, substituted or unsubstituted alkynyl, linear or branched, substituted or unsubstituted heteroalkynyl, substituted or unsubstituted cycloalkyl, substituted or unsubstituted heterocycloalkyl, substituted or unsubstituted aryl, or substituted or unsubstituted heteroaryl, linear or branched, substituted or unsubstituted alkylaryl, linear or branched, substituted or unsubstituted heteroalkylaryl, each having up to 24, such as up to 20, alternatively up to 18 carbon atoms;

wherein R, $R_x$, $R^1$, $R^2$, $R^3$, $R^4$, $R^5$ and $R^6$ are substituents independently selected from the group consisting of a linear or branched, substituted or unsubstituted alkyl, linear or branched, substituted or unsubstituted heteroalkyl, linear or branched, substituted or unsubstituted alkenyl, linear or branched, substituted or unsubstituted heteroalkenyl, linear or branched, substituted or unsubstituted alkynyl, linear or branched, substituted or unsubstituted heteroalkynyl, substituted or unsubstituted cycloalkyl, substituted or unsubstituted heterocycloalkyl, substituted or unsubstituted aryl, or substituted or unsubstituted heteroaryl, linear or branched, substituted or unsubstituted alkylaryl, linear or branched, substituted or unsubstituted heteroalkylaryl, each having up to 24, such as up to 20, alternatively up to 18 carbon atoms;

wherein "〜〜〜" is the DNA identifier tag as defined herein; and wherein "aryl" is as defined herein.

In non-limiting embodiments, "〜〜〜" is a linear or branched, substituted or unsubstituted alkyl having up to 20 carbon atoms or a bond.

The term "alkyne-aldehyde-amine three component reaction", as used herein, refers to a chemical reaction, wherein the educts

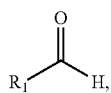 (1)

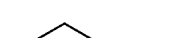 (2)

 (3)

are converted to

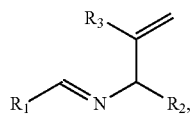

wherein $R_1$, $R_2$ and $R_3$ are as $R^1$, $R^2$ and $R^3$, defined above, and wherein at least one of $R_1$, $R_2$ or $R_3$ comprises the DNA identifier tag as described herein. In non-limiting embodiments, the catalyst used in the alkyne-aldehyde-amine three component reaction is Au(I).

The term "3+2 cycloaddition of azomethine ylides with dipolarophiles", as used herein, refers to a chemical reaction, wherein the educts

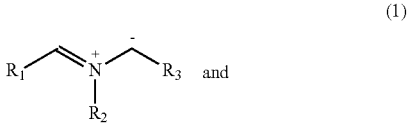 (1)

-continued

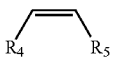
(2)

are converted to

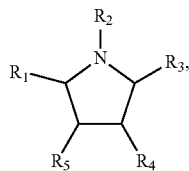

wherein $R_1$, $R_2$, $R_3$, $R_4$ and $R_5$ are as $R^1$, $R^2$, $R^3$, $R^4$ and $R^5$, defined above, and wherein at least one of $R_1$, $R_2$, $R_3$ $R_4$ or $R_5$ comprises the DNA identifier tag as described herein. In non-limiting embodiments, the catalyst used in the 3+2 cycloaddition of azomethine ylides with dipolarophiles is Ag(I) or Cu(I).

The term "oxidation of alcohols to aldehydes", as used herein, refers to a chemical reaction, wherein a molecule having a (terminal) alcohol group and comprising the linker group and the DNA identifier tag as defined above is oxidized to a molecule having a (terminal) aldehyde group and comprising the linker group and the DNA identifier tag as defined above. Said reaction, specifically its educts and products, are defined in H. Sand, R. Weberskirch, RSC Adv. 2015, 5, 38235-38242, which is herewith incorporated by reference. In non-limiting embodiments, the oxidation of alcohols to aldehydes is catalyzed by Cu(II).

The term "ring closing metathesis", as used herein, refers to a chemical reaction, wherein two terminal alkenes are reacted to form a cycloalkane. At least one of the two alkenes and the cycloalkane comprise the linker group and the DNA identifier tag as described above. In non-limiting embodiments, the ring closing metathesis is catalyzed by Cu(II).

The term "synthesis of indazoles by C—H bond functionalization/addition/cyclization cascades", as used herein, refers to a chemical reaction, wherein a terminal aldehyde comprising the linker group and the DNA identifier tag is reacted with an aniline derivative as described in Table 1 to form an indazole derivative comprising the linker group and the DNA identifier tag as described in Table 1. In non-limiting embodiments, the synthesis of indazoles by C—H bond functionalization/addition/cyclization cascades is catalysed by Co(III).

The term "aldol reaction", as used herein, refers to a chemical reaction of two educts selected from the group consisting of an aldehyde and a carbonyl group comprising compound, wherein at least one of the educts comprises the DNA identifier tag and the linker group as described herein to form a β-hydroxy carbonyl compound (aldol) comprising the DNA identifier tag and the linker group. In non-limiting embodiments, the aldol reaction is catalyzed by secondary or tertiary amines.

The term "Boc-deprotection", as used herein, refers to a chemical reaction in which an N-tert-butoxycarbonyl comprising compound that additionally comprises the DNA identifier tag and the linker group to form an amine that comprises the DNA identifier tag and the linker group. In non-limiting embodiments, the Boc-deprotection is catalyzed by alkane sulfonic acids or benzene sulfonic acids.

The "Pictet-Spengler reaction" is a chemical reaction in which a β-arylethylamine, such as tryptamine, undergoes ring closure after condensation with an aldehyde or ketone. Therefore, the educts are β-arylethylamine and aldehydes or ketones, wherein at least one of the educts comprises the DNA identifier tag and the linker group. The generated heterocycles also comprise the DNA identifier tag and the linker group. In non-limiting embodiments, the Pictet-Spengler reaction is catalyzed by alkane sulfonic acids or benzene sulfonic acids.

The term "Diels-Alder reaction", as used herein, refers to a chemical reaction wherein a conjugated diene and a substituted alkene are reacted to form a substituted cyclohexene. At least one of the educts and the substituted cyclohexene product comprise the DNA identifier tag and the linker group. In non-limiting embodiments, the substituent is nitrogen. In other non-limiting embodiments, the substituted alkene is a compound as described in Table 1. Further, in other alternative embodiments, the Diels-Alder reaction is catalyzed by Yb(III) or thioureas.

In various embodiments, the method further comprises ligating the first DNA identifier tag of the chimeric conjugate molecule to a second DNA identifier tag.

"Ligating", as used herein, refers to joining of separate single stranded polynucleotides to each other to form a single molecule. This is commonly but not exclusively achieved by means of a ligase. The term "DNA ligase," as used herein, refers to a family of enzymes, which catalyze the formation of a covalent phosphodiester bond between two distinct DNA strands, i.e. a ligation reaction. Two prokaryotic DNA ligases, namely the ATP-dependent T4 DNA ligase (isolated from the T4 phage), and the NAD$^+$-dependent DNA ligase from E. coli, have become indispensable tools in molecular biology applications. Both enzymes catalyze the synthesis of a phosphodiester bond between the 3'-hydroxyl group of one polynucleic acid, and the 5'-phosphoryl group, of a second polynucleic acid, for instance at a nick between the two strands, which are both hybridized to a third DNA strand. The mechanism of the ligation reaction catalyzed by this family of enzymes typically requires three enzymatic steps. The initial step involves attack of the α-phosphoryl group of either ATP or NAD resulting in formation of a ligase-adenylate intermediate (AMP is covalently linked to a lysine residue of the enzyme), and concurrent release of either pyrophosphate ($PP_i$) or nicotinamide mononucleotide (NAD$^+$). In the second step of the enzymatic reaction, AMP is transferred to the 5' end of the free 5' phosphate terminus of one DNA strand, to form an intermediate species of DNA-adenylate. In the final step, ligase catalyzes the attack of the DNA-adenylate intermediate species by the 3' hydroxyl group of the second DNA strand, resulting in formation of a phosphodiester bond and sealing of the nick between the two DNA strands, and concurrent release of AMP. RNA ligases, which are a related family of enzymes, catalyze the ligation of nicked RNA ends hybridized on to RNA or DNA in an analogous fashion. T4 DNA ligase is commercially available from at least USB and New England Biolabs. An RNA ligase can readily ligate a single strand DNA to a single strand RNA at the 3' end of the RNA. An RNA ligase can also readily ligate a 5' end of an RNA to a 3' end of an RNA. The ligation reactions described herein are generally achieved by means of a ligase such as available commercially and described in the New England Biolabs, Inc. catalog. Ligases include ATP-requiring RNA ligases such as a T4 RNA ligase 1 and T4 RNA ligase 2 truncated and mutants of T4 RNA ligase 2 as described in the examples.

In various other embodiments, the first and/or second DNA identifier tag is at least 4 nucleotides, such as at least 5 nucleotides, at least 6 nucleotides, at least 10 nucleotides or at least 14 nucleotides in length.

In still various other embodiments, the first DNA identifier tag is covalently linked to the small organic candidate compound by a linker group, such as a poly(ethylene glycol) linker group.

The term "linker" or "linker group", as interchangeably used herein, refers to any agent or molecule that bridges the first DNA identifier tag to the small organic candidate compound. This linker may be removed from said molecule by chemical means, by enzymatic means, or spontaneously. In some embodiments, the linker may be pharmacologically inert or may itself provide added beneficial pharmacological activity. The term "spacer" may also be used interchangeably as a synonym for linker. Linkers used in the present disclosure may include, for example, lipids, polypeptides, oligonucleotides, polymers, and the like. More than one linker may be used. For example, a first linker may be attached to the first DNA identifier tag followed by a second linker that is attached to the first linker. A third linker may be attached to the second linker and so on and so forth.

In various embodiments, the first DNA identifier tag or the linker group is covalently linked to the small organic candidate compound by amide bonds.

In further embodiments, the first small organic molecule has a log P (partition coefficient) value above 0.

In various embodiments, the second small organic molecule has a log P (partition coefficient) value above 0.

"Partition coefficient" or "P", as interchangeably used herein, refers to the coefficient, which is defined by the ratio of chemical activity or the concentrations of a compound in two or more phases of a multi-phase system at equilibrium. For example, the partition coefficient (P) of an analyte in a two-phase system can be defined as the ratio of the concentration of analyte in the first phase to that in the second phase. For multi-phase systems, there can be multiple partition coefficients, where each partition coefficient defines the ratio of species in a first selected phase and a second selected phase. It will be recognized that the total number of partition coefficients in any multi-phase system will be equal to the total number of phases minus one. The partition coefficient is meant to be octanol/water partition coefficient, if the phases of the system are not explicitly indicated. The logarithm of the ratio is thus "log P". When one of the solvents is water and the other is a non-polar solvent, such as octanol, then the log P value is a measure of lipophilicity or hydrophobicity. The defined precedent is for the lipophilic and hydrophilic phase types to always be in the numerator and denominator, respectively;

for example, in a biphasic system of n-octanol (hereafter simply "octanol") and water:

$$\log P_{oct/wat} = \log\left(\frac{[\text{solute}]_{octanol}^{un-ionized}}{[\text{solute}]_{water}^{un-ionized}}\right)$$

In non-limiting embodiments, the log P value of the first small organic molecule is above 0, above 0.5, above 1, above 1.5, above 2, above 2.5, above 3, above 3.5, above 4, above 4.5, above 5, above 5.5 or above 6.

While the second organic molecule may be similarly hydrophobic as the first small molecule, it is not as essential, as a high concentration thereof may ensure that the second small molecule also enters the micelle. In non-limiting embodiments, the second organic molecule is hydrophobic enough that at least a substantial portion thereof, such as at least 10% of the total number of molecules locates within the micelle. The portion located in the micelle is higher. In non-limiting embodiments, the log P value of the second small organic molecule is also above 0, above 0.5, above 1, above 1.5, above 2, above 2.5, above 3, above 3.5, above 4, above 4.5, above 5, above 5.5 or above 6.

In various embodiments, the first small organic molecule is an (hetero)aromatic organic moiety, such as an aromatic moiety, alternatively a phenyl moiety, wherein the (hetero) aromatic moiety is substituted with at least one halogen substituent, such as bromine or iodine. In non-limiting embodiments, the first organic moiety is a phenyliodide moiety.

Unless otherwise indicated, the term "hetero-aromatic", as used herein alone or as part of another group, refers to a 5- or 6-membered aromatic ring which includes 1, 2, 3 or 4 heteroatoms such as nitrogen, oxygen, or sulfur, and such rings fused to an aryl, cycloalkyl, heteroaryl or cycloheteroalkyl ring (e.g. benzothiophenyl, indole), and includes possible N-oxides. Hetero-aromatics may be optionally substituted with one to four substituents such as any of the alkyl or aryl substituents set out above. Examples of heteroaryl groups include the following:

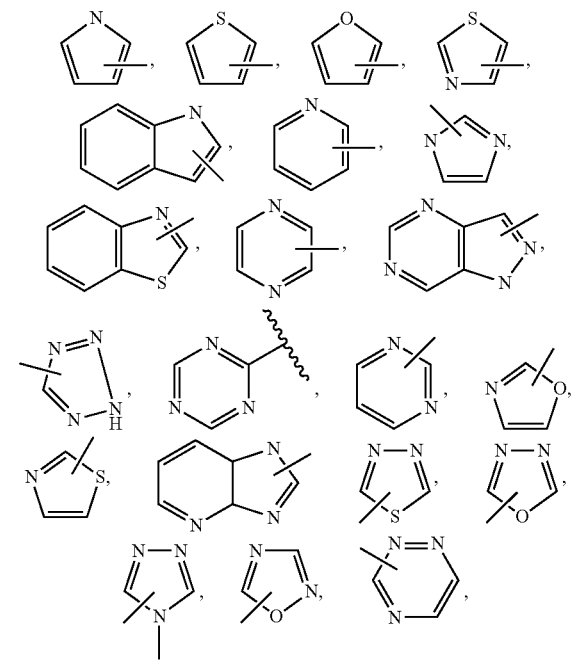

and the like.

The term "aromatic moiety", as used herein, is to be understood in accordance with its art-recognized scope, which includes substituted and unsubstituted mono- and polynuclear moieties. Moieties of an aromatic character, which possess a heteroatom, are also useful.

Substituted aromatic compounds, which may be used for the disclosure should possess at least one hydrogen atom directly bonded to the aromatic nucleus. The aromatic rings may be substituted with one or more alkyl, aryl, alkaryl, alkoxy, aryloxy, cycloalkyl, and halide.

Suitable aromatic moieties that may be used for this disclosure include benzyl, naphthyl, anthryl, naphthacenyl, perylenyl, coronenyl, and phenanthrenyl.

Suitable alkyl substituted aromatic moieties that may be used for this disclosure include toluenyl, xylenyl, isopropylbenzyl, propylbenzyl, alpha-methylnaphthyl, ethylbenzyl, mesitylenyl, durenyl, butylbenzyl, pseudocumenyl, o-diethylbenzyl, m-diethylbenzyl, p-diethylbenzyl, isoamylbenzyl, isohexylbenzyl, pentaethylbenzyl, pentamethylbenzyl, 1,2,3,4-tetraethylbenzyl, 1,2,3,5-tetramethylbenzyl, 1,2,4-triethylbenzyl, 1,2,3-trimethylbenzyl, m-butyltoluenyl, p-butyltoluenyl, 3,5-diethyltoluenyl, o-ethyltoluenyl, p-ethyl toluenyl, m-propyltoluenyl, 4-ethyl-m-xylenyl, dimethylnaphthyl, ethylnaphthyl, 2,3-dimethylanthracenyl, 9-ethylanthracenyl, 2-methylanthracenyl, o-methylanthracenyl, 9,10-dimethylphenanthrenyl, and 3-methyl-phenanthrenyl. Higher molecular weight alkylaromatic hydrocarbons may also be used and include aromatic hydrocarbons such as those that are produced by the alkylation of aromatic hydrocarbons with olefin oligomers. Such products are frequently referred to in the art as alkylate and include hexylbenzyl, nonylbenzyl, dodecylbenzyl, pentadecylbenzyl, hexyltoluenyl, nonyltoluenyl, dodecyltoluenyl, pentadecytoluenyl, etc.

The term "phenyl", as used herein, encompasses the unsubstituted phenyl radical or a phenyl radical which is substituted by any radical or radicals which are not reactive or otherwise interfering under the conditions or reaction, such as lower alkyl, lower alkoxy, trifluoromethyl, bromo, chloro, fluoro, nitro, and the like. The substituted phenyl radicals have no more than one to three substituents such as those given above and furthermore, these substituents can be in various available positions of the phenyl nucleus and, when more than one substituent is present, can be the same or different and can be in various position combinations relative to each other. The lower alkyl and lower alkoxy substituents each have from one to 24 carbon atoms, which can be arranged as straight or branched chains. Examples of the substituents are methyl, ethyl, propyl, butyl, fluoro, bromo, iodo, chloro, methoxy, ethoxy, propoxy, butoxy, and trifluoromethyl radicals.

In still various other embodiments, the second organic molecule is selected from the group consisting of organic boronic acids or boronic acid esters, such as (hetero)aromatic boronic acids or boronic acid esters, alkenes or alkynes. In non-limiting embodiments, the second organic molecule is selected from the group consisting of pyrimidine ring containing boronic acids, thiophene containing boronic acids and arylboronic acids.

The term "organo bromic acid", as used herein, refers to an organic acid, such as lactic acid (2-hydroxypropionic acid), succinic acid, furandicarboxylic acid, fumaric acid, maleic acid, citric acid, glutamic acid, aspartic acid, acrylic acid, oxalic acid, and glucanic acid, which comprises at least one bromo substituent. The term "organo bromic ester", as used herein, refers to an organic ester, such as organic groups formed by the reaction of a carboxylic acid and an alcohol, which comprises at least one bromo substituent. In non-limiting embodiments, the organic bromic acid and/or the organic bromic ester contains one bromo substituent.

In various embodiments of the method, the amphiphilic block copolymer comprises poly(styrene-co-N-vinylimidazole) as the hydrophobic block.

In still various embodiments of the method, the amphiphilic block copolymer comprises poly(acrylic acid ester), poly(acrylic acid) or poly(acrylamide).

In various embodiments, the catalyst is a transition metal catalyst, such as palladium, or an acidic group, such as sulfonic acid. In non-limiting embodiments, the catalyst is an N-heterocyclic carbine palladium complex.

The term "transition metal", as used herein, is a synonym for elements of the groups 3 to 12 of modern IUPAC numbering. Examples of transition metals are copper (Cu), silver (Ag), and gold (Au).

An "acidic group", as used herein, means a group, which can accept a pair of electrons to form a coordinate bond and a basic group as used herein means a group, which can donate a pair of electrons to form a coordinate bond.

In various embodiments, the reaction between the first and second small organic molecule is a Suzuki reaction or a Heck reaction.

The term "Suzuki reaction", as used herein, refers to a coupling reaction, where the coupling partners are a boronic acid and an organohalide catalyzed by a palladium(O) or palladium(II) complex.

The term "Heck reaction", as used herein, is the chemical reaction of an unsaturated halide (or triflate) with an alkene in the presence of a base and a palladium catalyst (or palladium nanomaterial-based catalyst), such as a palladium (O) or palladium(II) complex, to form a substituted alkene.

In various other embodiments, subjecting the reaction mixture to conditions that allow micelle formation and formation of the chimeric conjugate molecule is carried out at elevated temperature greater than or equal to 20° C., such as ≥40° C., alternatively ≥50° C., alternatively ≥60° C., but below 95° C. in a non-limiting embodiment.

In still various other embodiments, subjecting the reaction mixture to conditions that allow micelle formation and formation of the chimeric conjugate molecule is carried out for a time period of at least 1, such as at least 2, alternatively at least 4 hours.

In various embodiments, the second small organic molecule is used in at least 50 fold, alternatively at least 80 fold, at least 100 fold, at least 120 fold, at least 150 fold, at least 180 fold or at least 200 fold molar excess relative to the first small organic molecule.

In further embodiments, purifying the chimeric conjugate molecule occurs by chromatography or by precipitation.

The term "chromatography", as used herein, includes any molecular separation technique that involves a molecule or molecules interacting with a matrix. The matrix may take the form of solid or porous beads, resin, particles, membranes, or any other suitable material. Unless otherwise specified, chromatography includes both flow-through and batch techniques. The term "chromatography column", as used herein, refers to a component containing a chromatography matrix, and configured such that a mobile phase, e.g., a fluidic sample or buffer, can pass through the column, thereby passing through the matrix retained in the column. Chromatography also comprises multidimensional chromatography referring to the use of multiple separation mechanisms (for example, see "J. C. Giddings (1990), Use of Multiple Dimensions in Analytical Separations, in Hernan Cortes Editor, Multidimensional Chromatography: Techniques and Applications (1st ed. pp. 1), New York, N.Y.: Marcel Dekker, Inc.). Examples of liquid chromatography methods include, but are not limited to HPLC or GPC.

The term "precipitation", as used herein, refers to an insoluble compound from a solution contained in a container, wherein the insoluble compound, nucleated within the solution phase, "falls down" upon the surface of the container.

In further aspect, a micelle may have an outer hydrophilic portion and an inner hydrophobic portion, comprising (a) a plurality of amphiphilic block copolymer molecules, each comprising a hydrophilic block and a hydrophobic block, wherein the hydrophilic blocks of the plurality of amphiphilic block copolymer molecules form the outer hydrophilic portion of the micelle and the hydrophobic blocks of the plurality of amphiphilic block copolymer molecules form the inner hydrophobic portion of the micelle; and (b) a chimeric conjugate molecule comprising a small organic candidate compound, wherein said small organic candidate compound is obtainable by reacting a first small organic molecule with a second small organic molecule, covalently conjugated to a first DNA identifier tag, wherein the small organic candidate compound is in contact with the inner hydrophobic portion and the first DNA identifier tag is in contact with the outer hydrophilic portion.

As used herein, "micelle" refers to an aggregate of surfactant molecules comprising a hydrophobic interior. A normal micelle is a micelle in which the micelle has a hydrophilic outer shell and a hydrophobic inner core. Micelle formation occurs as a result of two forces. One is an attractive force that leads to the association of molecules, while the other is a repulsive force that prevents unlimited growth of the micelles to a distinct macroscopic phase. The micelle has an outer hydrophilic shell and an inner hydrophobic core. Polymeric micelles have a small particle size (<200 nm). Polymeric micelles are characterized by a core-shell structure. Polymeric micelles may have an X-Y diblock structure with X, the hydrophilic shell moieties and Y the hydrophobic core polymers. Multiblock copolymers such as poly(ethylene oxide)-poly(propylene oxide)-poly(ethylene oxide) (PEO-PPO-PEO) (X-Y-X) can also self-organize into micelles, and have been described in the art (FEBS Lett. 258 (1989) 343-345).

The term "outer portion", as used herein in the context of the micelle, refers to the surface layer of the micelle that is in direct contact with the continuous phase. The term "portion", as used herein in the context of the micelle, refers to the layer of the micelle that is not in direct contact with the continuous phase and that is surrounded by the outer portion.

"Plurality", as used herein, is defined as two or more than two, in particular 2, 3, 4, 5, 6, 7, 8, 9, 10 or more, alternatively 100 or more, 500 or more, 1000 or more, 1500 or more, 3000 or more, 5000 or more, 10000 or more or 50000 or more. "One or more", as used herein, is defined as one, two or more than two, in particular 1, 2, 3, 4, 5, 6, 7, 8, 9, 10 or more, alternatively 100 or more, 500 or more, 1000 or more, 1500 or more, 3000 or more, 5000 or more, 10000 or more or 50000 or more.

In a third aspect, a dispersion composition may include (a) one or more of the micelles and (b) an aqueous phase, wherein the aqueous phase is the continuous phase.

As used herein, "dispersion" relates to a 2-phase system with a first phase, the dispersed phase, being emulgated or suspended within a liquid continuous phase. The dispersed phase may be a solid insoluble in or a liquid immiscible with the continuous phase. The dispersed phase may be the micelles. The dispersion can thus be considered to represent an oil-in-water (o/w) emulsion. The dispersion may be stable, i.e. does not separate into 2 separate phases over a useful time period, for example, minutes, hours, days, etc.

The term "sequence", as used herein, relates to the primary nucleotide sequence of nucleic acid molecules or the primary amino acid sequence of a protein.

It is understood that all combinations of the above disclosed embodiments are also intended to fall within the scope of the present claims. It is further intended that all embodiments disclosed herein in relation to the methods similarly apply to the compounds, libraries, micelles and dispersions and vice versa.

EXAMPLES

Example 1

Preparation of Starting Materials and Positive Control

With the idea of protecting the DNA from the catalyst, it was hypothesized that a hydrophilic spacer moiety (a PEG-linker) between the DNA tag and the small molecule would ensure the DNA from having any interactions with the catalyst immobilized in the hydrophobic core of the micelle (FIG. 1). The starting material for the Suzuki reaction without a PEG-linker was also synthesized in order to investigate the importance of the spacer for the reaction. Also, a positive reference molecule was synthesized in order to compare the reaction product during characterization (FIG. 2).

Figure 2:
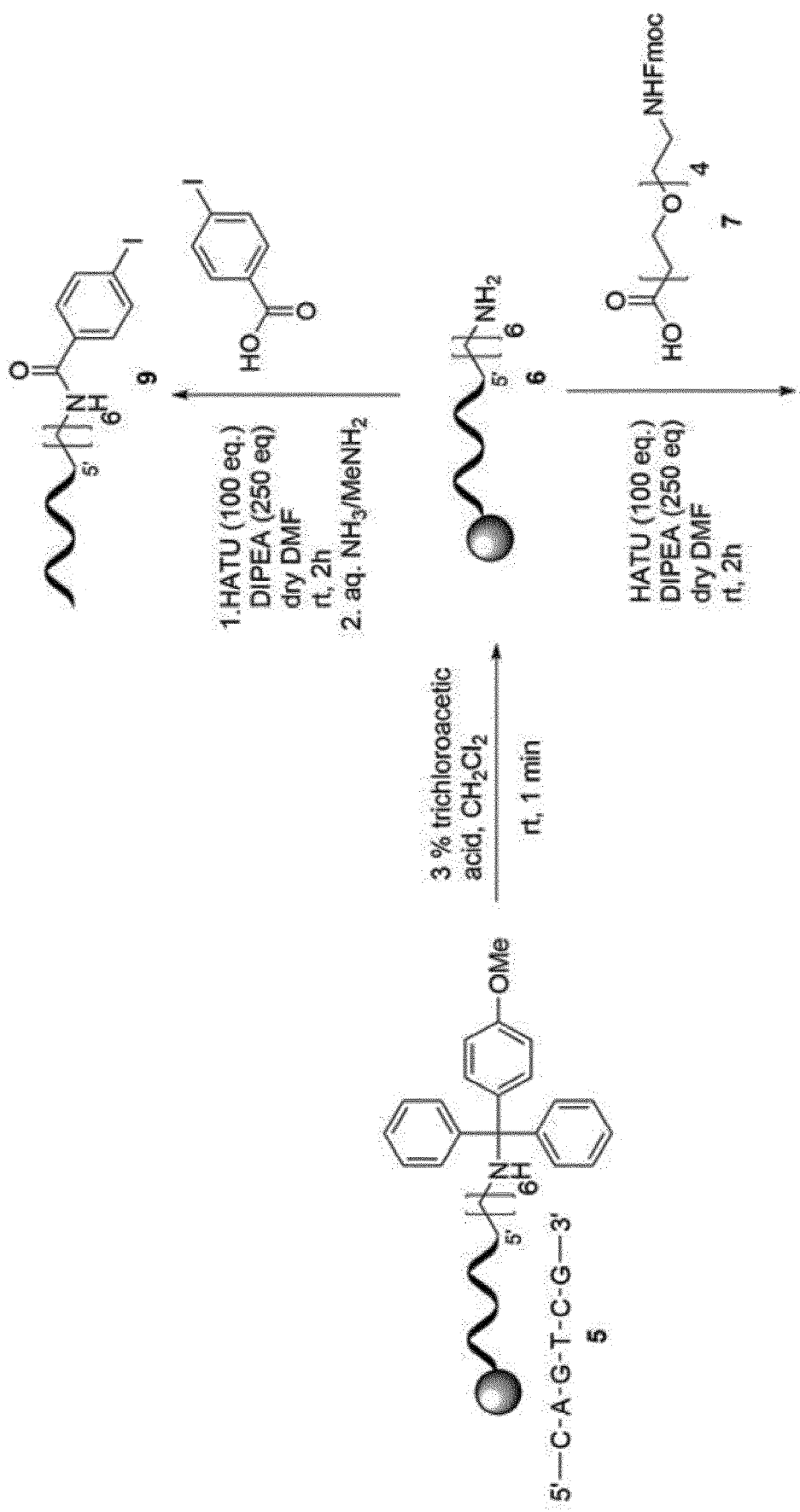
FIG. 2 shows a synthesis scheme for the preparation of starting material by amide coupling.
Figure 2:
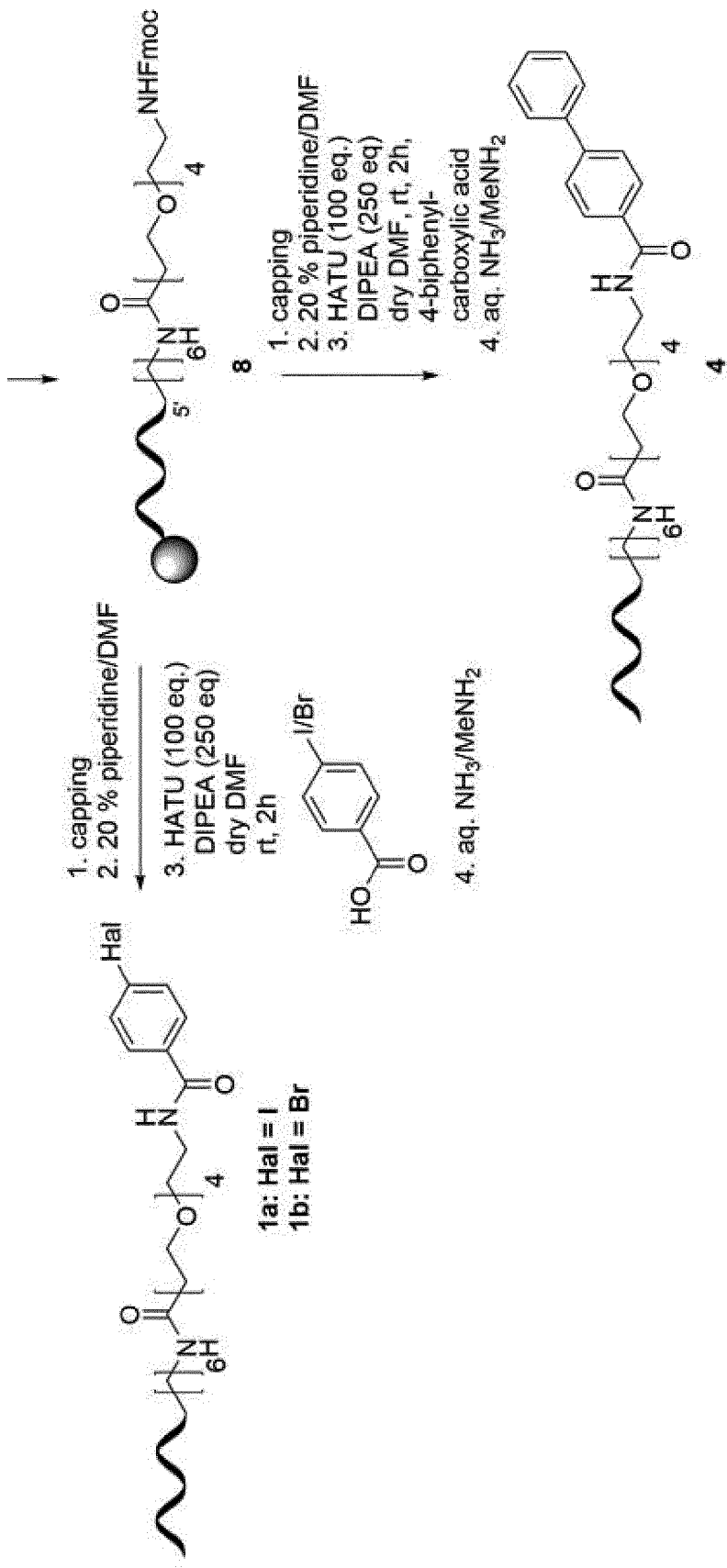
Figure 3:
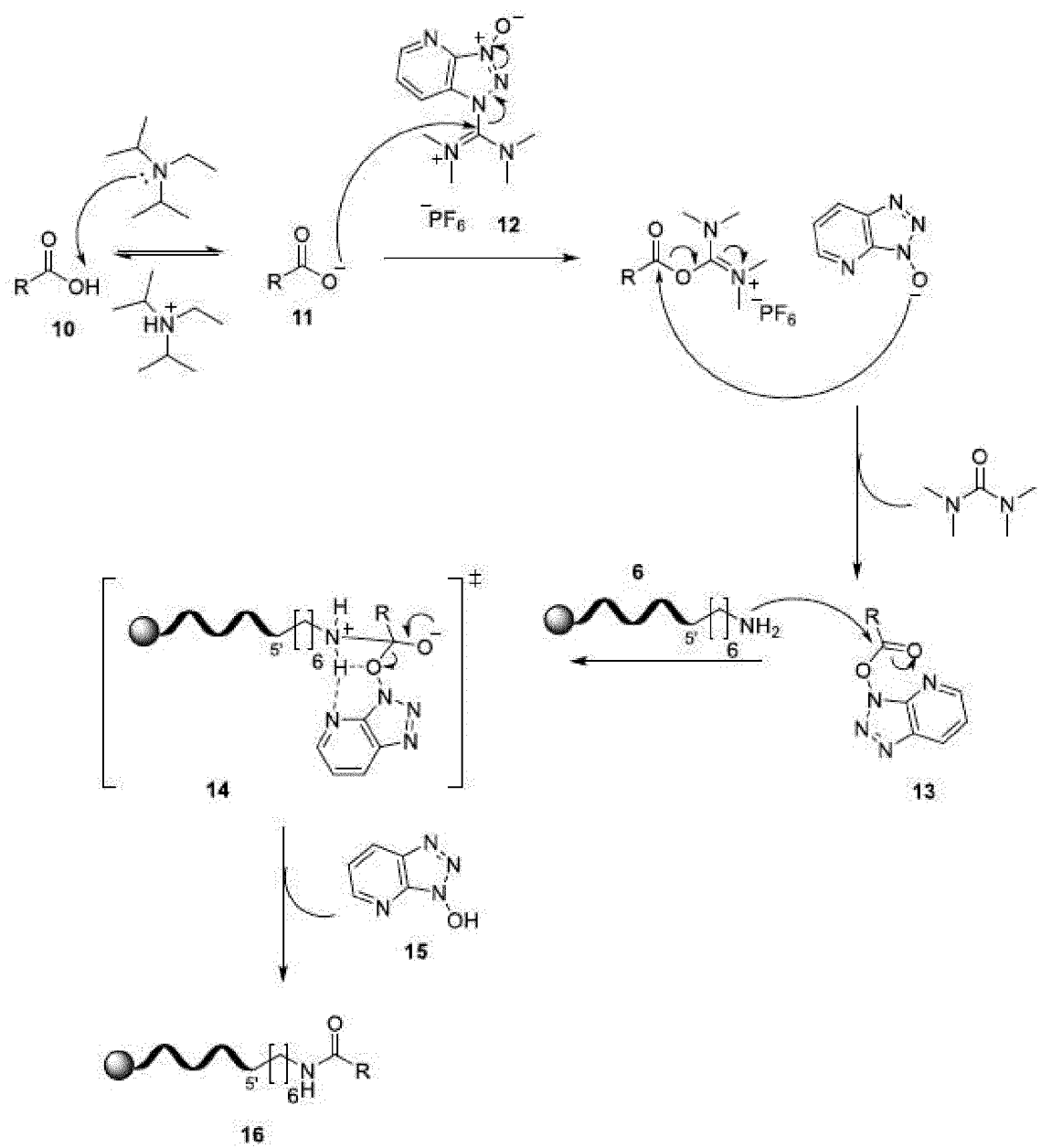
FIG. 3 shows the mechanism of the amide bond formation using HATU as the coupling reagent.

Hence, the first set of starting materials (6 and 7) synthesized had a polyethylene glycol coupled to the C-6 amino linker at the 5'-end of the oligonucleotide sequence (FIG. 2). The deprotection of the oligonucleotide adapter 5 could be observed by the formation of a monomethoxytrityl cation, which showed an intensively orange colour. When the colour could not be observed anymore, the deprotection was complete and an amide coupling with 6-amino-hexyl-5'-(3'-(dCdAdGdTdCdG)-5') hydrogen phosphate 6 and a carboxylic acid could be performed. The amide coupling mediated by HATU 12 which forms an active ester 13 with a deprotonated carboxylic acid 11 (FIG. 3). After a nucleophilic substitution of the primary amine of the 5'-amino-C6-linker 6 an amide bond is formed. Using the PEG-linker 7 as the carboxylic acid, the PEGylated DNA-conjugate 8 was prepared.

Figure 4:
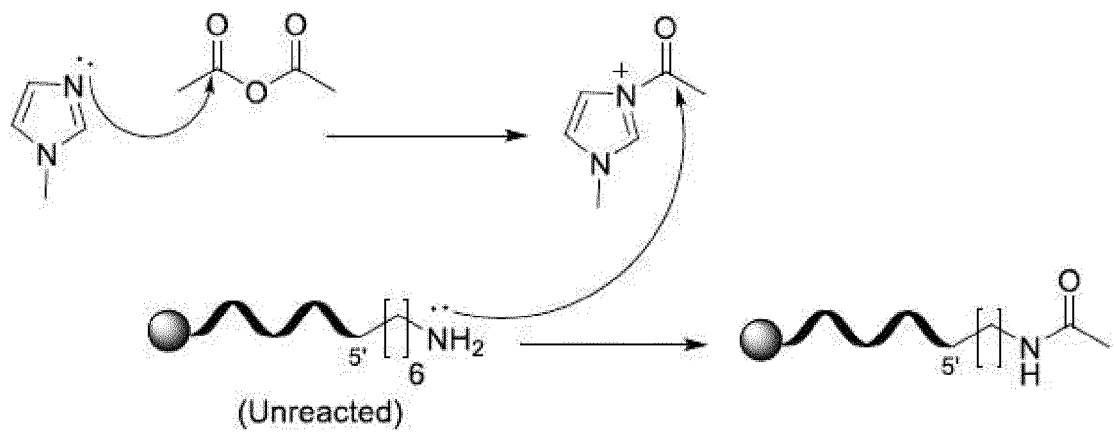
FIG. 4 shows the capping of unreacted starting material 6.

Alternatively, the deprotected 6-amino-hexyl-5'-(3'-(dCdAdGdTdCdG)-5') hydrogen phosphate 6 was also coupled with p-iodobenzoic acid (FIG. 2) to the starting material without a PEG-linker 8. Subsequently with conjugate 8, further amide coupling was done to attach p-iodo/p-bromobenzoic acid in the same manner as described previously. But for subsequent amide couplings to be performed, it is necessary to block the unreacted primary amine from 6, before the second amide coupling. This is done over a capping step with acetic anhydride, pyridine and methylimidazole in dry THF (FIG. 4).

After the capping step, the amine group of the PEGylated conjugate 8 is protected by a fluorenylmethyloxycarbonyl (Fmoc) group, since the PEG(4)-carboxylic acid 7 is delivered from a commercial source having an Fmoc protected amine group to avoid polymerization. This Fmoc group is deprotected by a 20% piperidine solution in DMF. Deprotection of the Fmoc group followed by the second amide coupling step produces the starting materials 1a and 1b and the positive reference molecule 4. After cleaving the oligonucleotides from the solid support, they were characterized using HPLC and MALDI-TOF mass spectrometry.

The MALDI MS spectra of the starting materials and the positive control show a series of peaks of decreasing intensity following the peak corresponding to the actual mass of the DNA-conjugate. All these peaks have a difference of ~23 units between them and they correspond to the peaks where sodium ions bind to the phosphate part of the oligonucleotides (data not shown).

Example 2

Identification of the Appropriate Analysis Method

Prior to the optimization of reaction conditions of the micellar catalyzed Suzuki reaction, there was a necessity to identify the appropriate method of analyzing the reaction. The problem at hand was the presence of at least a hundred-fold excess of the boronic acid and cesium carbonate each, and the presence of the polymer.

HPLC

During the first attempt, the reaction mixture was diluted with water and directly injected into the HPLC column and the following problems were observed:

1. Phenylboronic acid eluted very close to the starting material 1a; and
2. The micelle forming polymer sticks to the column and contaminates the column making it necessary to wash the column thoroughly after each analysis.

MALDI-TOF Mass Spectrometry

After the HPLC method was rendered inefficient as the analysis method for further work on this reaction, the next option was mass spectrometry. Similar to the previous experiment, the reaction mixture was directly spotted on the MALDI-MS target plate with 2',4',6'-trihydroxyacetophenone (THAP) and ammonium citrate as the matrix mixture. The result was an extremely disturbed mass spectrum, which has been observed as a typical spectrum when there is a presence of excessive impurities. Since no conclusions can be drawn from such a MALDI-MS spectrum, a purification of the DNA sample may be crucial for a robust analysis.

Example 3

DNA Sample Purification

DNA Precipitation

Figure 5:
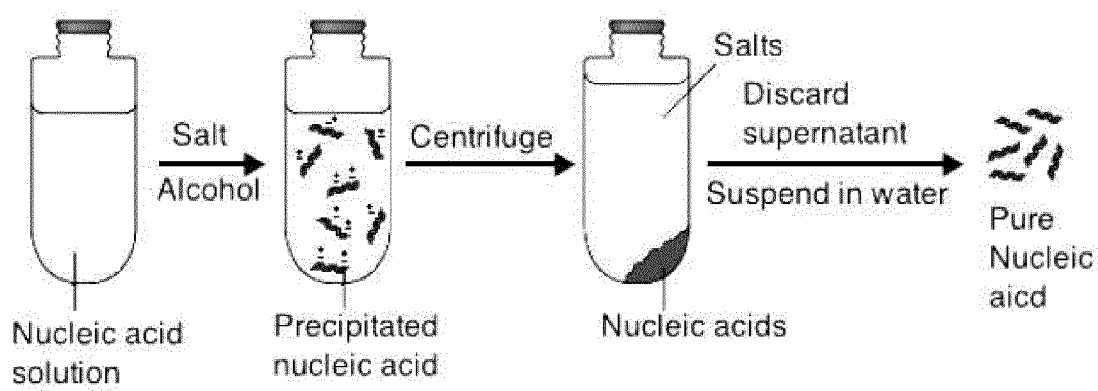
FIG. 5 shows an illustration of DNA precipitation.

DNA is polar due to its phosphate backbone making it water soluble. But ethanol being much less polar than water, it can facilitate the formation of ionic bonds between the phosphate groups of the DNA and a positively charged ion (FIG. 5), causing the DNA to precipitate.

By precipitating the DNA, it was assumed that the (relatively) less polar phenylboronic acid and the micellar polymer would stay dissolved in ethanol while DNA precipitates out of the ethanol solution. But unfortunately, it was found that there was still a considerable amount of contaminants along with the DNA precipitate, which was disturbing the MALDI-MS spectrum. Hence, it may be required to further purify the DNA sample before putting it on the MALDI-MS target plate.

ZipTip

The ZipTip is a 10 µL pipette tip with a bed of chromatography media fixed at its end. It is intended for purifying very small quantities of oligonucleotide samples prior to analysis, providing better data quality. Using the ZipTips it was possible to obtain a clear mass spectrum, which could be used for further analysis (data not shown). Furthermore, the reaction mixture was washed with ethylacetate to remove as much phenylboronic acid as possible before the precipitation step.

This method was laborious since the precipitation step usually took more than 6-8 hours and the ZipTip procedure was a challenging process, if a large number of samples was analyzed. Hence, it may represent an efficient way to purify the DNA sample while synthesizing a library. Since, one aim was the development of a robust working procedure to use the micellar catalyzed Suzuki reaction for synthesizing a DNA-encoded library, it may be desirable to find another method of DNA-purification, which can be prepared quickly and easily.

Glen-Pak™

Figure 6:
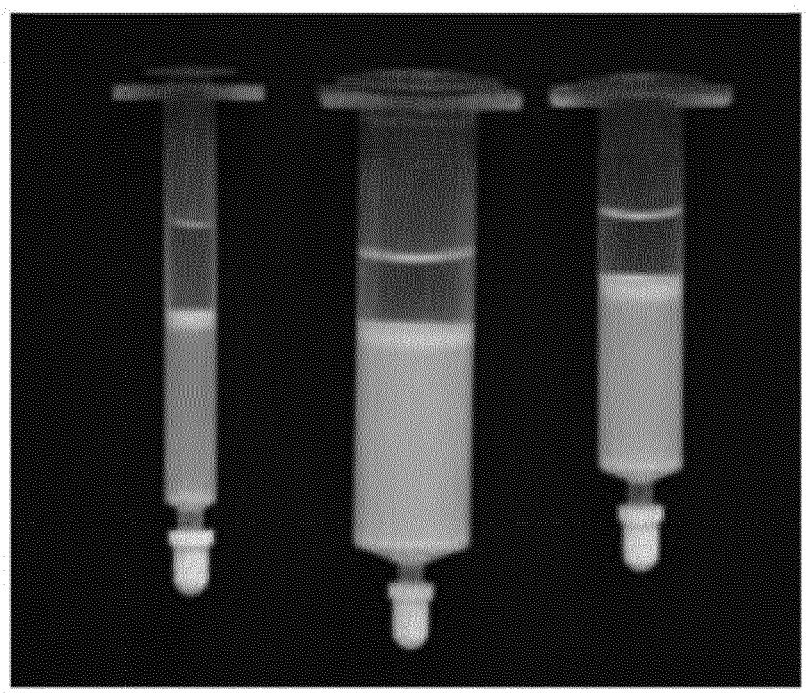
FIG. 6 shows a picture of the Glen-Pak™ cartridge.

Glen-Pak™ is basically a 3-5 micron sized polydivinylbenzene packing material (FIG. 6), which are stable to dilute ammonium hydroxide or ammonium hydroxide/methylamine (AMA). It works on the same principle as ZipTip, that is, the DNA is first bound to the polymer resin, the contaminants are washed away and the purified DNA sample is then eluted out of the resin.

With the use of Glen-Pak™, it was possible to skip the precipitation step and therefore, the reaction mixture after washing with ethyl acetate could directly be injected into the Glen-Pak™ cartridge. By eluting the DNA, it was possible to directly analyze the sample by MALDI-MS without the use of ZipTips. Thus, with this method of purification it was possible to establish a robust analysis method. Furthermore, this purification method could facilitate the use of HPLC for analyzing the reaction.

Example 4

Optimization of Reaction Conditions

Figure 7:
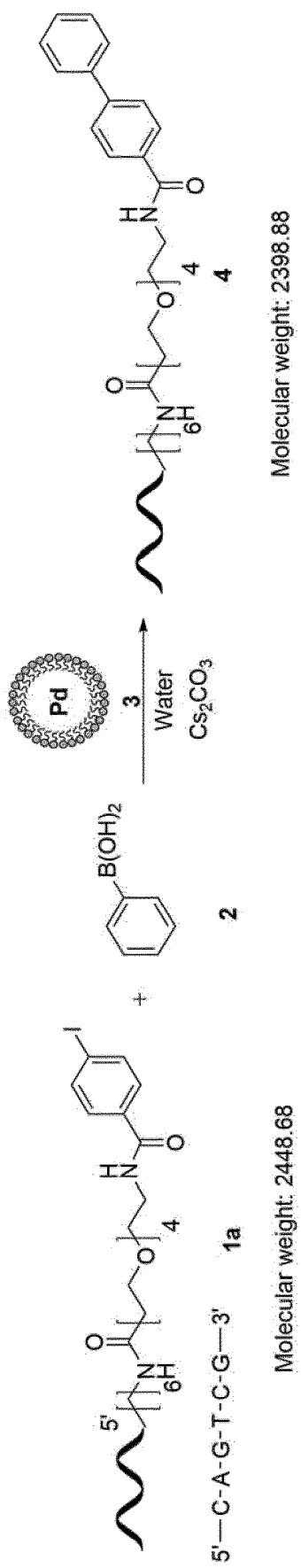
FIG. 7 shows the micellar catalyzed Suzuki reaction of the hexamer DNA-phenyliodide conjugate 1a with phenylboronic acid 2 to give the DNA-biphenyl conjugate 4 catalyzed using the micelle-forming Pd catalyst 3.

With the optimized ZipTip procedure for analysis, the next step was the optimization of the micellar catalyzed Suzuki reaction (FIG. 7). For the optimization of the reaction conditions, the dependency of four factors on the conversion of the starting material to the product, namely 1) amount of boronic acid; 2) amount of base; 3) temperature; and 4) time, was analyzed.

In a system without a DNA tag, it was found that cesium carbonate was the mildest and best base to be used for the Suzuki reaction.

A table of the reaction conditions and approximate conversion percentages is given below in FIG. 8 (numbers 1, 2 and 4 refer to FIG. 7).

Dependency on Temperature

The reaction shows a clear dependency on temperature (FIG. 8). This temperature dependency can be observed at 50 equivalent excess of the boronic acid. While the conversion of the starting material to the product is very low at room temperature, a linear increase in conversion is observed with increasing temperature. The oxidative addition step of the Suzuki coupling being the rate determining step, can sometimes require elevated temperatures to occur. This is because the palladium changes from an oxidation state of 0 to an oxidation state of +2.

Dependency on Time

The reaction demonstrates a clear dependency on time (FIG. 8). The dependency can be observed at 50 equivalent excess of the boronic acid.

Dependency on Amount of Boronic Acid

The reaction demonstrates a clear dependency on the amount of boronic acid (FIG. 8). The amount of boronic acid also affects other parameters such as time and temperature. This can be seen from FIG. 8 at a 500-fold excess of boronic acid, where almost all reaction conditions show nearly complete conversion. Such phenomena may be explained by the statistical increase in the number of phenylboronic acid molecule entering the micellar core and getting involved in the catalytic cycle.

The dependence on the base was not significant and it can be seen that the conversion of starting material to product hardly changes, when the amount of base was changed from 100 eq. excess to 200 eq. excess.

Negative Control Experiments

As negative control conditions, the reaction was conducted without each of the components of the reaction, namely the base, the boronic acid and the micelle forming polymer. Additionally, the reaction was also conducted with the micellar polymer at a concentration below the CMC to examine the importance of the micellar formation (data not shown).

As expected, the reaction does not occur without any one of the components and the starting material 1a remains non-reacted. It is also interesting to note that the reaction does not occur without the formation of the micelles (data not shown).

Example 5

Scope of the Reaction and the Catalytic System

Screening of Boronic Acids/Esters (Substrate Scope)

Figure 9:
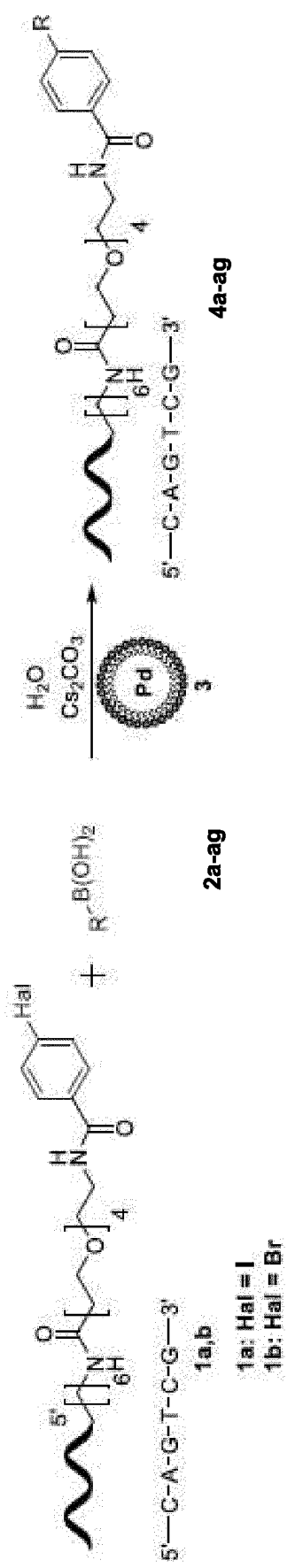
FIG. 9 shows the screening of boronic acids/esters.

After establishing a reliable analysis method and optimizing the reaction conditions for the Suzuki coupling reaction using catalyst immobilized micellar catalysis, it was necessary to examine the substrate scope of this reaction. For this purpose, 33 boronic acids and boronic acid esters (2a-ag) were screened with the DNA conjugates (1a and 1b) to get the expected products 4a-ag (FIGS. 9 and 10).

Figure 10:
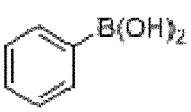
FIG. 10 shows the screened boronates 2a-ag.
Figure 10:
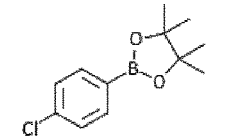
Figure 10:
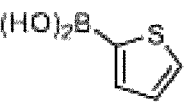
Figure 10:
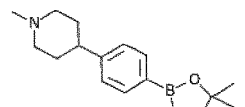
Figure 10:
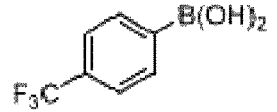
Figure 10:
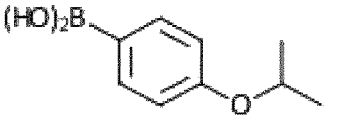
Figure 10:
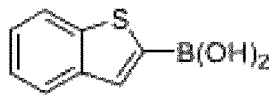
Figure 10:
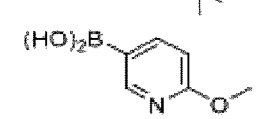
Figure 10:
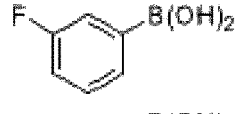
Figure 10:
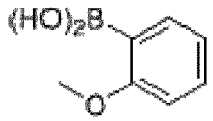
Figure 10:
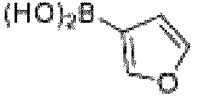
Figure 10:
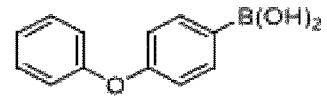
Figure 10:
Figure 10:
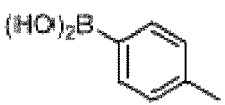
Figure 10:
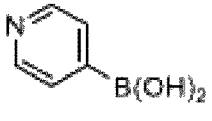
Figure 10:
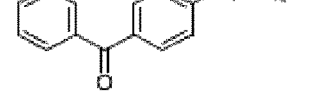
Figure 10:
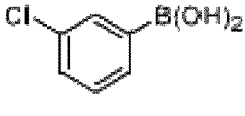
Figure 10:
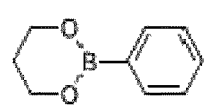
Figure 10:
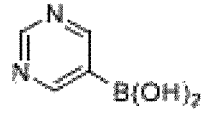
Figure 10:
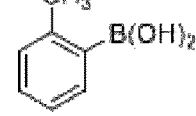

It can be observed that the catalytic system is versatile in terms of substrate scope (FIG. 10). Since the reactions are done in water, the immediate problem that arises is the inability of several boronic acids to dissolve in water. To overcome this issue, highly hydrophobic boronic acids and boronic ester (boronates) were dissolved in toluene. It was observed that the hydrophobic boronic acids/boronates migrate to the water phase and enter the core of the micelle to undergo the reaction. Therefore, the possibility to use toluene as a co-solvent expanded the substrate scope of the reaction.

Substrates with a water soluble group such as a pyrimidine ring have shown complete conversion to the product (entry 2o), which shows that incubation for a longer period of time can cause the slight hydrophobic character of the molecules to enter the hydrophobic core of the micelles. Thiophene containing boronic acid has shown complete conversion to the product, which is usually not possible with simple palladium catalysts, showing the versatility of this particular catalytic system. Other notable observations are that at the optimized reaction condition the arylboronic acids with a strongly electron withdrawing group also undergo full conversion to the product (entries 2c, 2d, 2ae, 2ag of FIG. 10); arylboronic acid/esters with a chloro-group do not show a side product where the Suzuki reaction occurs with the chloro-group, which has been observed for NHC-Palladium catalysts.

Substrates 2l and 2ab show a partial conversion of the starting material to the product. 2l does not undergo complete conversion because of the substrate's inability to solubilize completely in water or toluene and 2ab shows partial conversion probably because it only partially enters the micelle in equilibrium.

Reaction Without the PEG-Linker

Figure 11:
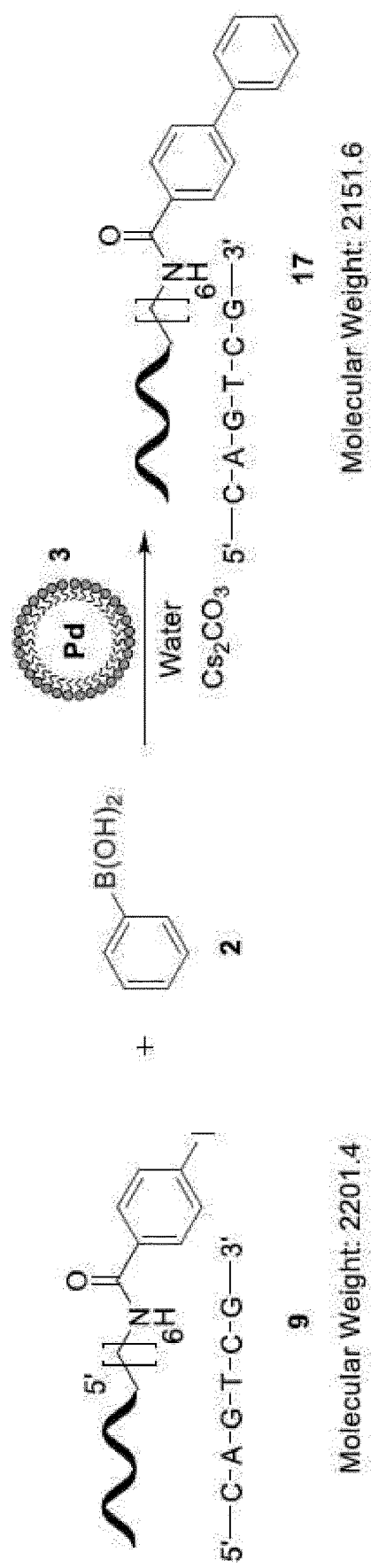
FIG. 11 shows the Suzuki reaction without a PEG-linker.

The reaction was initially planned to be conducted with a hydrophilic PEG(4) spacer between the DNA and the hydrophobic small molecule to make sure that the catalyst doesn't come in contact with the DNA. But the importance of this spacer was examined by synthesizing a DNA-small molecule conjugate without a PEG-linker (molecule 9 of FIG. 11). As shown in FIG. 11, the DNA-conjugate without a PEG-linker 9, was used to conduct the reaction to get the product 17.

The reaction was feasible and there was no damage to the DNA-tag. The PEG-linker idea was retained in further experiments, but the result that the same system can be used even without the PEG-linker provides insight on the versatility of the reaction.

Other Palladium Catalyzed Reactions

Figure 12:
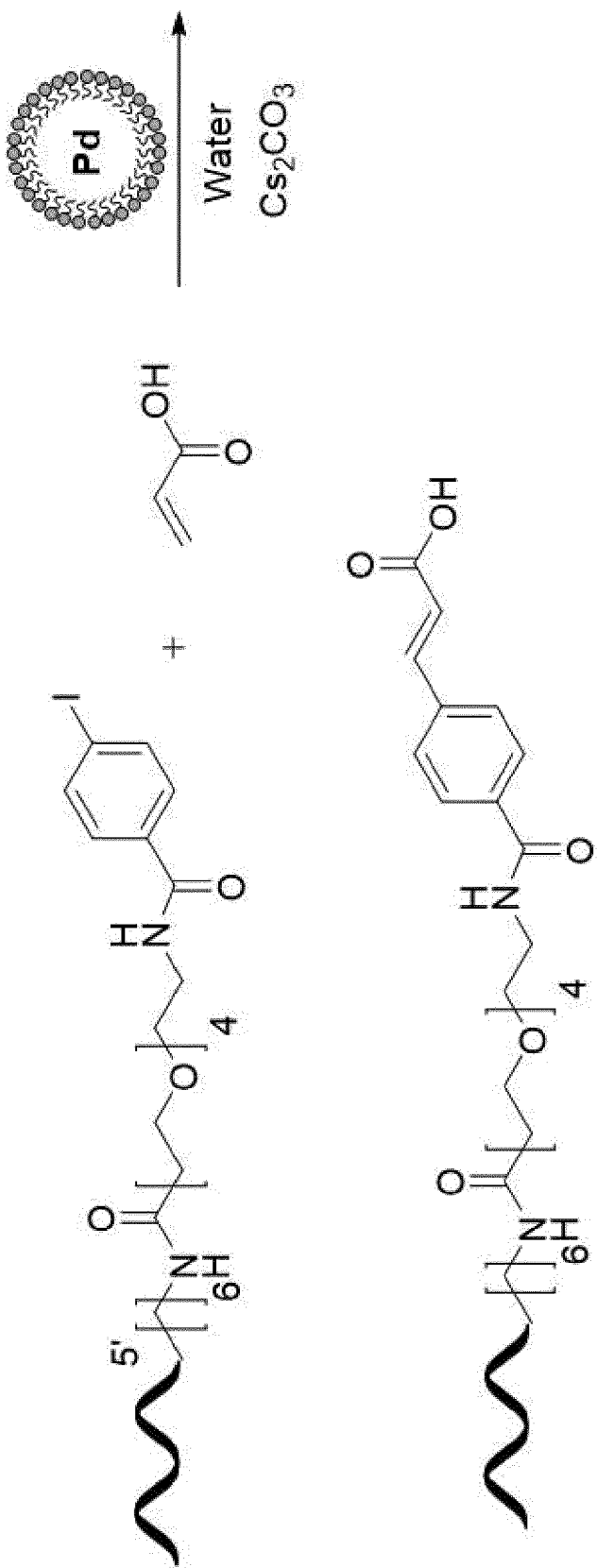
FIG. 12 shows the Heck reaction with acrylic acid.
Figure 13:
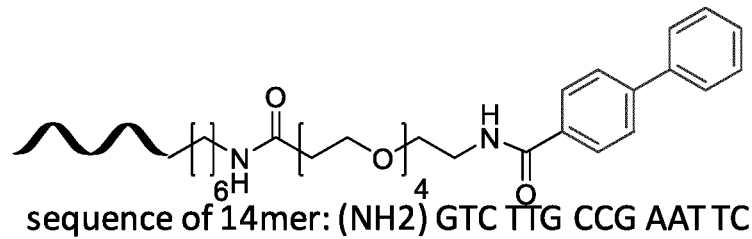
FIG. 13 shows the product of micellar catalyzed Suzuki reaction of the 14mer DNA-phenyliodide conjugate with phenylboronic acid 2 to give the depicted DNA-biphenyl conjugate catalyzed using the micelle-forming Pd catalyst 3, and MALDI-MS spectra of the product.
Figure 13:
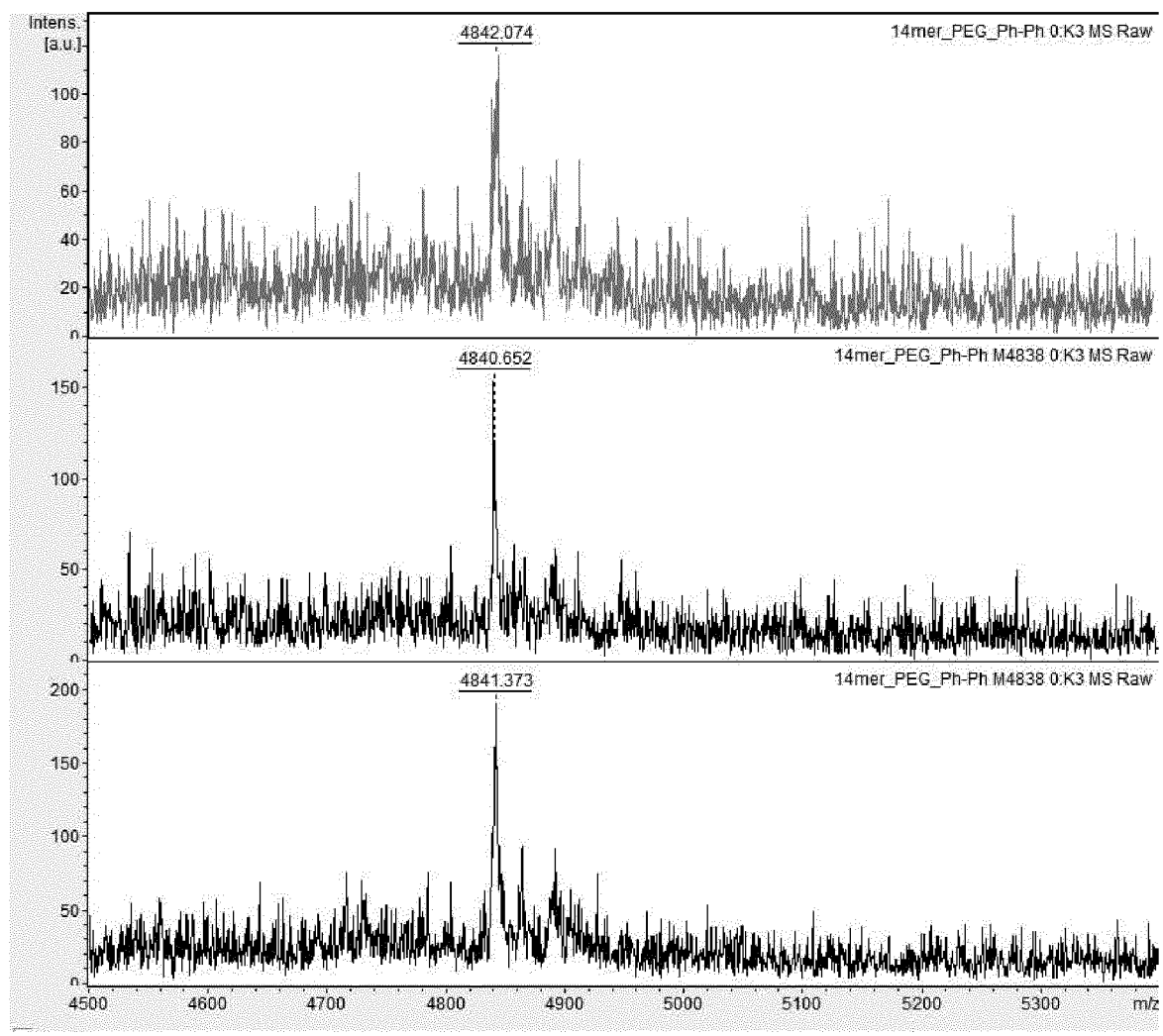

NHC-palladium catalyst is a stable catalyst system against air, moisture, etc., and also a very versatile catalyst system for various palladium catalyzed reactions. Hence, another palladium catalyzed reaction was set up using this catalytic system, namely the Heck reaction (FIG. 12). It was observed that the Heck reaction occurred partially (data not shown).

Example 6

Sulphonic Acid Immobilized Micelle

Figure 14:
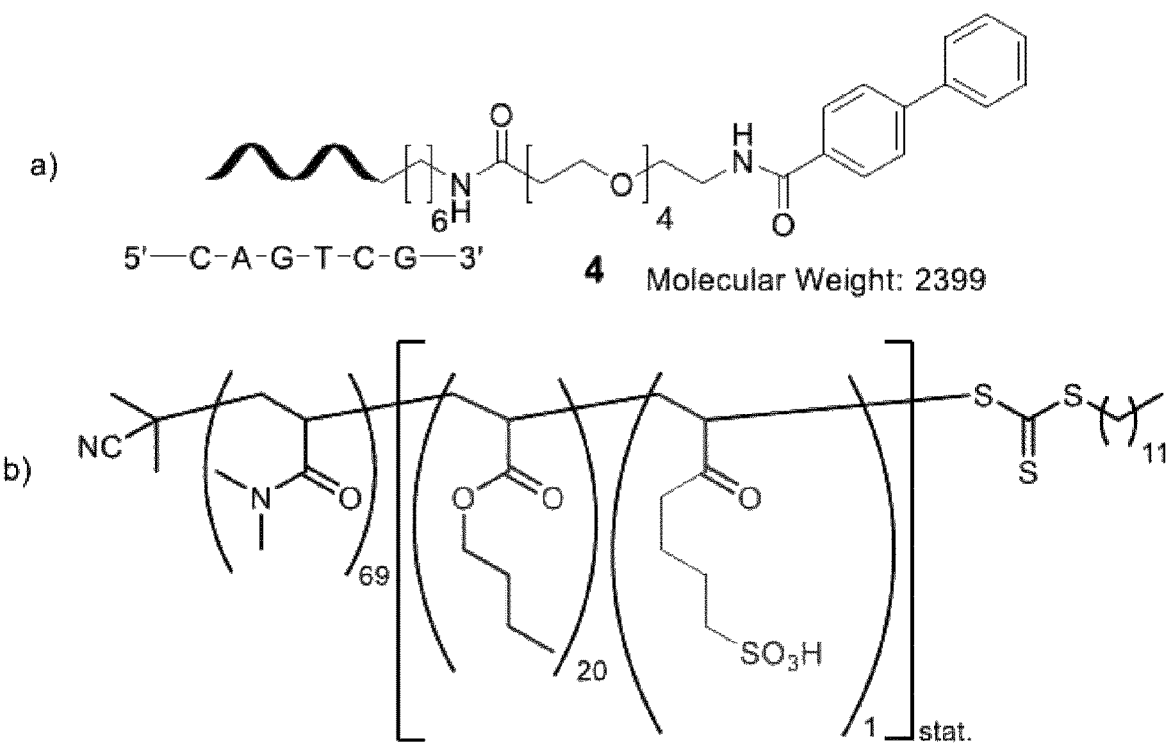
FIG. 14a) shows DNA-conjugate 4; b) structure of the sulphonic acid immobilized amphiphilic block copolymer.

An amphiphilic block copolymer (ABC) with a sulphonic acid immobilized in the hydrophobic core (FIG. 14b) was examined for its interactions with a DNA-small molecule conjugate. Acidic environments cause depurination of the DNA. Hence, possible interactions between the sulphonic acid on the ABC and the DNA were investigated.

For this purpose, the DNA-conjugate 4 (FIG. 14a) was incubated with 40 µL of a 2% TFA solution (~10 nmol of TFA in the solution) in one Eppendorf tube and with 10 µL of a 1 mM solution of the ABC (10 nmol of the micelle) in another Eppendorf tube. It has to be noted that the CMC of the ABC is 1 µM and hence a 1 mM solution of it was used. After incubating the DNA-conjugate with the two solutions for 18 hours, the DNA-samples were purified by a ZipTip and placed on the MALDI-MS target plate for analysis.

By analyzing the mass spectrum of the two samples, it was observed that the DNA-conjugate 4 incubated with the 2% TFA solution had undergone depurination and there was no trace of the mass signal corresponding to the original mass of 2399. Instead, the peaks corresponding to depurination were observed. On the other hand, the DNA-conjugate 4 incubated with the micellar solution showed no peaks corresponding to depurination and the entire molecule was intact (data not shown).

In the DNA-conjugate 4, there are three purines, 2 guanines and 1 adenine. It can be observed that the mass corresponding to the removal of guanine 2267 (calculated mass=2263) is the smallest peak, the removal of the second guanine corresponding to mass 2149 (calculated mass=2136) is the largest peak. This reflects the expected trend that guanine groups undergo depurination more feasibly. Also, another peak corresponding to removal of the adenine at a mass of 2016 (calculated mass=2011) is observed. The DNA-conjugate incubated with the micellar solution undergoes no change and hence it can be concluded that the sulphonic acid does not interact with the DNA. Moreover, this also acts as a proof for the concept of shielding the DNA from a catalyst immobilized in the micelle (data not shown).

All documents cited herein, are hereby incorporated by reference in their entirety.

The methods illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims. Thus, it should be understood that although the present invention has been specifically disclosed by non-limiting embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A method for the synthesis of a chimeric conjugate molecule by micellar catalysis; wherein the method comprises:
    forming a reaction mixture comprising:
        a conjugate starting molecule comprising a first small organic molecule covalently conjugated to a first DNA identifier tag;
        the second small organic molecule that is to be reacted with the first small organic molecule covalently linked to the first DNA identifier tag to yield the chimeric conjugate molecule;
        an amphiphilic block copolymer comprising a hydrophilic block and a hydrophobic block; wherein the hydrophobic block is functionalized with a catalyst that catalyzes the reaction between the first small organic molecule and second small organic molecule; wherein the amphiphilic block copolymer is added in an amount that the final concentration of the amphiphilic block copolymer in the reaction mixture is greater than a critical micelle concentration (CMC) of said amphiphilic block copolymer; and
        an aqueous solvent;
    subjecting the reaction mixture to conditions that allow micelle formation of the amphiphilic block copolymer and to allow formation of the chimeric conjugate molecule from the reaction between the first and second small organic molecule in the interior of the micelle; and
    purifying the chimeric conjugate molecule from the reaction mixture.

2. The method according to claim 1, further comprising ligating the first DNA identifier tag of the chimeric conjugate molecule to a second DNA identifier tag.

3. The method according to claim 2, wherein the first DNA identifier tag and/or the second DNA identifier tag comprises at least 4 nucleotides in length.

4. The method according to claim 1, wherein the first DNA identifier tag is covalently linked to the small organic candidate compound by a linker group.

5. The method according to claim 4, wherein the first DNA identifier tag or the linker group is covalently linked to the small organic candidate compound by amide bonds.

6. The method according to claim 1, wherein the first small organic molecule has a log P (partition coefficient) value above 0.

7. The method according to claim 1, wherein the second small organic molecule has a log P (partition coefficient) value above 0.

8. The method according to claim 1, wherein the first small organic molecule is an (hetero)aromatic organic moiety substituted with at least one halogen substituent.

9. The method according to claim 1, wherein the amphiphilic block copolymer comprises poly(styrene-co-N-vinylimidazole) as the hydrophobic block.

10. The method according to claim 1, wherein the amphiphilic block copolymer comprises poly(acrylic acid ester), poly(acrylic acid), poly(acrylamide), or combinations thereof.

11. The method according to claim 1, wherein the catalyst is a transition metal catalyst, an acidic group, or combinations thereof.

12. The method according to claim 1, wherein the reaction between the first small organic molecule and the second small organic molecule is a Suzuki reaction or a Heck reaction.

13. The method according to claim 1, wherein the subjecting the reaction mixture to conditions that allow micelle formation and formation of the chimeric conjugate molecule is carried out at elevated temperature greater than or equal to 20° C.

14. The method according to claim 1, wherein the subjecting the reaction mixture to conditions that allow micelle formation and formation of the chimeric conjugate molecule is carried out for a time period of at least 1 hour.

15. The method according to claim 1, wherein the second small organic molecule is used in at least 50 fold relative to the first small organic molecule.

16. The method according to claim 1, wherein the catalyst is a N-heterocyclic carbine palladium complex.

* * * * *